United States Patent
Lerner et al.

(10) Patent No.: US 9,180,097 B2
(45) Date of Patent: Nov. 10, 2015

(54) FORMULATIONS OF 6-MERCAPTOPURINE

(71) Applicant: Teva Pharmaceutical Industries, Ltd., Petach-Tikva (IL)

(72) Inventors: E. Itzhak Lerner, Petach Tikva (IL); Moshe Flashner-Barak, Petach Tikva (IL); Erwin v. Achthoven, Leiderdorp (NL); Hans Keegstra, Alkmaar (NL); Ruud Smit, Haarlem (NL)

(73) Assignee: TEVA PHARMACEUTICAL INDUSTRIES LTD., Petach-Tikva (IL)

( * ) Notice: Subject to any disclaimer, the term of this patent is extended or adjusted under 35 U.S.C. 154(b) by 0 days.

(21) Appl. No.: 14/177,037

(22) Filed: Feb. 10, 2014

(65) Prior Publication Data

US 2014/0161888 A1    Jun. 12, 2014

Related U.S. Application Data

(60) Continuation of application No. 13/455,932, filed on Apr. 25, 2012, now Pat. No. 8,653,060, which is a division of application No. 11/097,874, filed on Apr. 1, 2005, now Pat. No. 8,188,067.

(60) Provisional application No. 60/558,477, filed on Apr. 1, 2004.

(51) Int. Cl.
    *A61K 31/33*     (2006.01)
    *A61K 31/52*     (2006.01)
    *A61K 31/522*    (2006.01)
    *A61K 9/16*      (2006.01)

(52) U.S. Cl.
    CPC .............. *A61K 9/1676* (2013.01); *A61K 9/1623* (2013.01); *A61K 9/1652* (2013.01); *A61K 9/1682* (2013.01); *A61K 31/52* (2013.01); *A61K 31/522* (2013.01)

(58) Field of Classification Search
    USPC .......................................... 514/263.1, 263.3
    See application file for complete search history.

(56) References Cited

U.S. PATENT DOCUMENTS

| | | | |
|---|---|---|---|
| RE23,082 E | 1/1949 | Zimmer et al. | |
| 2,697,708 A | 12/1954 | Hitchings et al. | |
| 3,163,639 A | 12/1964 | Hitchings et al. | |
| 3,548,782 A | 12/1970 | Cunningham et al. | |
| 4,059,706 A | 11/1977 | Pischke et al. | |
| 4,443,435 A | 4/1984 | Bodor et al. | |
| 4,749,706 A | 6/1988 | Lawson et al. | |
| 4,749,707 A | 6/1988 | Calvo et al. | |
| 5,053,499 A | 10/1991 | Kojima et al. | |
| 5,100,675 A | 3/1992 | Cho et al. | |
| 5,120,740 A | 6/1992 | Elfarra | |
| 5,200,417 A | 4/1993 | Brown et al. | |
| 5,229,131 A | 7/1993 | Amidon et al. | |
| 5,364,646 A | 11/1994 | Gruber et al. | |
| 5,370,744 A | 12/1994 | Chowhan et al. | |
| 5,389,380 A | 2/1995 | Noda et al. | |
| 5,691,343 A | 11/1997 | Sandborn | |
| 5,776,431 A | 7/1998 | Galat | |
| 6,323,193 B1 | 11/2001 | Somani et al. | |
| 6,355,623 B2 | 3/2002 | Seidman et al. | |
| 6,372,254 B1 | 4/2002 | Ting et al. | |
| 6,576,438 B2 | 6/2003 | Barstad | |
| 6,602,521 B1 | 8/2003 | Ting et al. | |
| 6,642,276 B2 | 11/2003 | Wadhwa | |
| 6,680,068 B2 | 1/2004 | Campbell et al. | |
| 6,692,771 B2 | 2/2004 | Pather et al. | |
| 6,740,162 B2 | 5/2004 | Huttlin | |
| 6,987,108 B2 | 1/2006 | Ugwu et al. | |
| 8,188,067 B2 | 5/2012 | Lerner et al. | |
| 8,653,060 B2 | 2/2014 | Lerner et al. | |
| 2002/0013287 A1 | 1/2002 | Sampath et al. | |
| 2002/0160049 A1 | 10/2002 | Pather et al. | |
| 2002/0164371 A1 | 11/2002 | Ting et al. | |
| 2003/0077306 A1 | 4/2003 | Pather et al. | |
| 2003/0133976 A1 | 7/2003 | Pather et al. | |
| 2003/0232760 A1 | 12/2003 | Garsky et al. | |
| 2004/0013728 A1 | 1/2004 | Oh et al. | |
| 2004/0043001 A1 | 3/2004 | Ugwu et al. | |
| 2005/0196418 A1 | 9/2005 | Yu et al. | |
| 2005/0277689 A1 | 12/2005 | Brook et al. | |
| 2006/0008520 A1 | 1/2006 | Lerner et al. | |
| 2006/0009473 A1 | 1/2006 | Lerner et al. | |
| 2007/0020306 A1 | 1/2007 | Schultheiss | |
| 2008/0020041 A1 | 1/2008 | Ayres | |
| 2009/0042914 A1 | 2/2009 | Lerner et al. | |
| 2009/0263482 A1 | 10/2009 | Rosenberger et al. | |

(Continued)

FOREIGN PATENT DOCUMENTS

| | | |
|---|---|---|
| AU | 2005232582 | 9/2009 |
| AU | 2005232583 | 9/2009 |
| GB | 833463 | 4/1960 |

(Continued)

OTHER PUBLICATIONS

Present, D.H. et al (NEJM vol. 302 pp. 981-987, published 1980).*
Radford-Smith, G.L. et al (The Lancet vol. 354, pp. 1386-1387, published 1999).*
Neurath, M.F. et al (Gut vol. 44 pp. 625-628 published 1999).*
Lee, W.A. et al., (Pharmaceutical Research vol. 7, pp. 161-166 1990).*
Takeichi, Y. et al (Biol. Pharm Bull. vol. 17, pp. 1391-1394, published 1994).*
Purinethol Prescribing Information (Published 2002).*
Present et al., NEJM vol. 302, pp. 981-987 (1980).*
Korelitz et al., American Journal of Gastroenterology vol. 94, pp. 3248-3253 (1999).*

(Continued)

*Primary Examiner* — Paul Zarek
*Assistant Examiner* — George W Kosturko
(74) *Attorney, Agent, or Firm* — John P. White; Gary J. Gershik; Cooper & Dunham LLP

(57) ABSTRACT

The present invention provides improved formulations of 6-mercaptopurine that exhibit better bioavailability and faster dissolution than previous formulations.

12 Claims, 4 Drawing Sheets

(56) References Cited

U.S. PATENT DOCUMENTS

| | | | |
|---|---|---|---|
| 2013/0280328 A1 | 10/2013 | Rosenberger et al. | |
| 2014/0370105 A1 | 12/2014 | Rosenberger et al. | |

FOREIGN PATENT DOCUMENTS

| | | | | |
|---|---|---|---|---|
| GB | 1203328 | * | 8/1970 | ............. A61K 27/00 |
| GB | 1203328 A2 | * | 8/1970 | |
| JP | 2003-518038 | | 6/2008 | |
| KR | 2000-0012706 | | 3/2000 | |
| KR | 0930309 | | 11/2009 | |
| MX | 274570 | | 3/2010 | |
| WO | WO 96/30021 | | 10/1996 | |
| WO | WO 00/69520 | | 11/2000 | |
| WO | WO 01/45677 | | 6/2001 | |
| WO | WO 2005/092638 | | 10/2005 | |
| WO | WO 2005/099665 | | 10/2005 | |
| WO | WO 2005/123061 | | 12/2005 | |
| WO | WO 2009/128955 | | 10/2009 | |

OTHER PUBLICATIONS

Jul. 17, 2007 Restriction Requirement issued in connection with U.S. Appl. No. 11/097,874.
Dec. 17, 2007 Response to Jul. 17, 2007 Restriction Requirement issued in connection with U.S. Appl. No. 11/097,874.
Feb. 5, 2008 Office Action issued in connection with U.S. Appl. No. 11/097,874.
Jul. 9, 2008 Amendment in response to Feb. 5, 2008 Office Action issued in connection with U.S. Appl. No. 11/097,874.
Nov. 7, 2008 Office Action issued in connection with U.S. Appl. No. 11/097,874.
Feb. 4, 2009 Amendment in response to Nov. 7, 2008 Office Action issued in connection with U.S. Appl. No. 11/097,874.
Apr. 23, 2009 Office Action issued in connection with U.S. Appl. No. 11/097,874.
Jul. 20, 2009 Amendment in response to Apr. 23, 2009 Office Action issued in connection with U.S. Appl. No. 11/097,874.
Sep. 24, 2009 Office Action issued in connection with U.S. Appl. No. 11/097,874.
Jan. 25, 2010 Amendment accompanying RCE in response to Sep. 24, 2009 Office Action issued in connection with U.S. Appl. No. 11/097,874.
Sep. 30, 2010 Office Action issued in connection with U.S. Appl. No. 11/097,874.
Mar. 3, 2011 Amendment in response to Sep. 30, 2010 Office Action issued in connection with U.S. Appl. No. 11/097,874.
Apr. 20, 2011 Office Action issued in connection with U.S. Appl. No. 11/097,874.
Sep. 2, 2011 Amendment in response to Apr. 20, 2011 Office Action issued in connection with U.S. Appl. No. 11/097,874.
Oct. 19, 2011 Office Action issued in connection with U.S. Appl. No. 11/097,874.
Jan. 11, 2012 Amendment in response to Oct. 19, 2011 Office Action issued in connection with U.S. Appl. No. 11/097,874.
Jan. 26, 2012 Notice of Allowance issued in connection with U.S. Appl. No. 11/097,874.
Feb. 12, 2013 Restriction Requirement issued in connection with U.S. Appl. No. 13/455,932.
Mar. 6, 2013 Amendment in response to Feb. 12, 2013 Restriction Requirement issued in connection with U.S. Appl. No. 13/455,932.
Apr. 19, 2013 Office Action issued in connection with U.S. Appl. No. 13/455,932.
Jul. 19, 2013 Amendment in response to Apr. 19, 2013 Office Action issued in connection with U.S. Appl. No. 13/455,932.
Oct. 10, 2013 Notice of Allowance issued in connection with U.S. Appl. No. 13/455,932.
Office Action dated Mar. 31, 2008 in connection with U.S. Appl. No. 11/097,875.
Jun. 13, 2008 Amendment in response to Office Action dated Mar. 31, 2008 in connection with U.S. Appl. No. 11/097,875.
Office Action dated Sep. 15, 2008 in connection with U.S. Appl. No. 11/097,875.
Jan. 14, 2009 Amendment in response to Office Action dated Sep. 15, 2008 in connection with U.S. Appl. No. 11/097,875.
Office Action dated Oct. 5, 2009 in connection with U.S. Appl. No. 11/097,875.
Jan. 5, 2010 Amendment accompanying RCE in response to Office Action dated Oct. 5, 2009 in connection with U.S. Appl. No. 11/097,875.
Office Action dated Mar. 31, 2010 in connection with U.S. Appl. No. 11/097,875.
Notice of Abandonment dated Oct. 13, 2010 in connection with U.S. Appl. No. 11/097,875.
Office Action dated Sep. 28, 2011 in connection with U.S. Appl. No. 12/215,941.
Notice of Abandonment dated Jun. 29, 2012 in connection with U.S. Appl. No. 12/215,941.
International Search Report dated Oct. 30, 2006 in connection with PCT International Application No. PCT/US2005/011112.
Written Opinion dated Dec. 5, 2008 in connection with PCT International Application No. PCT/US2005/011112.
International Search Report dated Oct. 19, 2006 in connection with PCT International Application No. PCT/US2005/011113.
Written Opinion dated Nov. 17, 2006 in connection with PCT International Application No. PCT/US2005/011113.
Office Action dated May 5, 2008 in connection with Australian Patent Application No. 2005232582.
Sep. 5, 2008 Response to Office Action dated May 5, 2008 in connection with Australian Patent Application No. 2005232582.
Office Action dated May 5, 2008 in connection with Australian Patent Application No. 2005232583.
Oct. 29, 2008 Response to Office Action dated May 5, 2008 in connection with Australian Patent Application No. 2005232583.
Official Action dated Aug. 13, 2008 in connection with Canadian Patent Application No. 2,560,654.
Oct. 9, 2008 Response to Official Action dated Aug. 13, 2008 in connection with Canadian Patent Application No. 2,560,654.
Official Action dated Oct. 6, 2009 in connection with Canadian Patent Application No. 2,560,654.
Feb. 10, 2010 Response to Official Action dated Oct. 6, 2009 in connection with Canadian Patent Application No. 2,560,654.
Official Action dated Nov. 3, 2008 in connection with Canadian Patent Application No. 2,560,997.
Feb. 3, 2009 Response to Official Action dated Nov. 3, 2008 in connection with Canadian Patent Application No. 2,560,997.
Official Action dated Jul. 9, 2009 in connection with Canadian Patent Application No. 2,560,997.
Nov. 18, 2009 Response to Official Action dated Jul. 9, 2009 in connection with Canadian Patent Application No. 2,560,997.
Office Action issued Dec. 12, 2008 in connection with Chinese Patent Application No. 200580016998.3.
Apr. 26, 2009 Response to Office Action issued Dec. 12, 2008 in connection with Chinese Patent Application No. 200580016998.3.
Office Action issued Feb. 5, 2010 in connection with Chinese Patent Application No. 200580016998.3.
Office Action issued Aug. 28, 2009 in connection with Chinese Patent Application No. 200580017148.5.
Mar. 10, 2010 Response to Office Action issued Aug. 28, 2009 in connection with Chinese Patent Application No. 200580017148.5.
Office Action issued Nov. 23, 2007 in connection with Eurasian Patent Application No. 200601596 (translation only).
Jul. 2, 2008 Response to Office Action issued Nov. 23, 2007 in connection with Eurasian Patent Application No. 200601596.
Office Action issued Dec. 15, 2008 in connection with Eurasian Patent Application No. 200601596 (translation only).
Office Action issued Nov. 22, 2007 in connection with Eurasian Patent Application No. 200601597 (translation only).
Aug. 20, 2008 Response to Office Action issued Nov. 22, 2007 in connection with Eurasian Patent Application No. 200601597.
Office Action issued Dec. 25, 2008 in connection with Eurasian Patent Application No. 200601597 (translation only).
Communication pursuant to Article 94(3) EPC issued Nov. 28, 2012 in connection with European Patent Application No. 05767549.8.

(56) References Cited

OTHER PUBLICATIONS

Mar. 26, 2013 Amendment in response to Communication pursuant to Article 94(3) EPC issued Nov. 28, 2012 in connection with European Patent Application No. 05767549.8.
Communication pursuant to Article 94(3) EPC issued Jul. 26, 2013 in connection with European Patent Application No. 05767549.8.
Jan. 22, 2014 Amendment in response to Communication pursuant to Article 94(3) EPC issued Jul. 26, 2013 in connection with European Patent Application No. 05767549.8.
Office Action dated Mar. 30, 2010 in connection with Japanese Patent Application No. JP 2007-506314.
Office Action dated Mar. 23, 2010 in connection with Japanese Patent Application No. JP 2007-506315.
Office Action dated Jun. 19, 2009 in connection with Mexican Patent Application No. PA/a/2006/011316 (translation only).
Sep. 2, 2009 Response to Office Action dated Jun. 19, 2009 in connection with Mexican Patent Application No. PA/a/2006/011316.
Office Action dated Sep. 10, 2009 in connection with Mexican Patent Application No. PA/a/2006/011316.
Dec. 2, 2009 Response to Office Action dated Sep. 10, 2009 in connection with Mexican Patent Application No. PA/a/2006/011316.
Jan. 14, 2010 Notice of Allowance in connection with Mexican Patent Application No. PA/a/2006/011316.
Office Action dated Jun. 18, 2009 in connection with Mexican Patent Application No. PA/a/2006/011317.
Sep. 28, 2009 Response to Office Action dated Jun. 18, 2009 in connection with Mexican Patent Application No. PA/a/2006/011317.
Notice of Allowance dated Oct. 8, 2009 in connection with Mexican Patent Application No. PA/a/2006/011317.
Office Action dated Sep. 6, 2007 in connection with South Korean Patent Application No. 10-2006-7020728.
Jun. 9, 2008 Amendment in response to Office Action dated Sep. 6, 2007 in connection with South Korean Patent Application No. 10-2006-7020728.
Office Action dated Oct. 9, 2008 in connection with South Korean Patent Application No. 10-2006-7020728.
Dec. 9, 2008 Response to Office Action dated Oct. 9, 2008 in connection with South Korean Patent Application No. 10-2006-7020728.
Office Action dated Apr. 13, 2009 in connection with South Korean Patent Application No. 10-2006-7020728.
Notice of Appeal From Final Rejection dated Apr. 13, 2009 in connection with South Korean Patent Application No. 10-2006-7020728.
Decision of Grant issued Sep. 2, 2009 in connection with South Korean Patent Application No. 10-2006-7020728.
Office Action dated Aug. 28, 2007 in connection with South Korean Patent Application No. 10-2006-7020725.
Jun. 30, 2008 Amendment in response to Office Action dated Aug. 28, 2007 in connection with South Korean Patent Application No. 10-2006-7020725.
Office Action dated Oct. 21, 2008 in connection with South Korean Patent Application No. 10-2006-7020725.
Feb. 4, 2009 Amendment in response to Office Action dated Oct. 21, 2008 in connection with South Korean Patent Application No. 10-2006-7020725.
Office Action dated Jun. 17, 2009 in connection with South Korean Patent Application No. 10-2006-7020725.
Aug. 17, 2009 Response to Office Action dated Jun. 17, 2009 in connection with South Korean Patent Application No. 10-2006-7020725.
Notice of Decision for Final Rejection dated Dec. 11, 2009 in connection with South Korean Patent Application No. 10-2006-7020725.
Mar. 12, 2010 Response to Notice of Decision for Final Rejection dated Dec. 11, 2009 in connection with South Korean Patent Application No. 10-2006-7020725.
Apr. 12, 2011 Office Action issued in connection with U.S. Appl. No. 12/386,611.
Aug. 9, 2011 Amendment in response to Apr. 12, 2011 Office Action issued in connection with U.S. Appl. No. 12/386,611.
Aug. 22, 2011 Office Action issued in connection with U.S. Appl. No. 12/386,611.
Nov. 22, 2011 Amendment in response to Aug. 22, 2011 Office Action issued in connection with U.S. Appl. No. 12/386,611.
Dec. 5, 2011 Office Action issued in connection with U.S. Appl. No. 12/386,611.
Apr. 17, 2012 Amendment in response to Dec. 5, 2011 Office Action issued in connection with U.S. Appl. No. 12/386,611.
Jun. 27, 2012 Office Action issued in connection with U.S. Appl. No. 12/386,611.
Aug. 7, 2013 Notice of Abandonment issued in connection with U.S. Appl. No. 12/386,611.
Jul. 22, 2013 Office Action issued in connection with U.S. Appl. No. 13/921,836.
Oct. 10, 2013 Amendment in response to Jul. 22, 2013 Office Action issued in connection with U.S. Appl. No. 13/921,836.
Jan. 13, 2014 Office Action issued in connection with U.S. Appl. No. 13/921,836.
Jul. 18, 2014 Notice of Abandonment issued in connection with U.S. Appl. No. 13/921,836.
International Search Report dated Jul. 23, 2009 in connection with PCT International Application No. PCT/US2009/002460.
Written Opinion dated Oct. 10, 2008 in connection with PCT International Application No. PCT/US2009/002460.
Official Action dated Feb. 23, 2012 in connection with Canadian Patent Application No. 2,271,728.
Aug. 22, 2012 Amendment in response to Official Action dated Feb. 23, 2012 in connection with Canadian Patent Application No. 2,271,728.
Official Action dated Nov. 21, 2012 in connection with Canadian Patent Application No. 2,271,728.
May 21, 2014 Amendment in response to Official Action dated Nov. 21, 2012 in connection with Canadian Patent Application No. 2,271,728.
European Search Report issued Jul. 23, 2009 in connection with European Patent Application No. 09005528.6.
Communication issued Nov. 16, 2009 in connection with European Patent Application No. 09005528.6.
Communication issued Mar. 11, 2011 in connection with European Patent Application No. 09005528.6.
Jan. 4, 2014 Amendment in response to Communication issued Mar. 11, 2011 in connection with European Patent Application No. 09005528.6.
Decision of Refusal issued Dec. 14, 2012 in connection with European Patent Application No. 09005528.6.
Best, W., et al., "Development of a Crohn's disease activity index: National cooperative Crohn's disease study," Gastroenterology, 70: 439-444 (1976).
Definition, "Coating", Oxford English Dictionary (online edition).
D'Haens, et al., "Early combined immunosuppression or Conventional Management in Patients with Newly Diagnosed Crohn's Disease: An Open Randomised Trial," Lancet, 371: 660-667 (2008).
D'Haens, et al., "Endoscopic and Histologic Healing of Crohn's (Ileo-)Colitis with Azathioprine," Gastrointestinal Endoscopy, 50: 667-671 (1999).
Elion, et al., "Studies on Condensed Pyrimidine Systems. IX. The Synthesis of Some 6-Substituted Purines," J. Am. Chem. Soc., 74(2): 411-414 (1952).
Faure et al., "Process control and scale-up of pharmaceutical wet granulation processes: a review" European Journal of Pharmaceutics and Biopharmaceutics, 52:269-277 (2001).
Friedman, S., et al., "General principles of medical therapy of inflammatory bowel disease," Gastroenterology Clinics of North America, 33: 191-208 (2004).
Fuss, I.J., et al., "Disparate CD4+ lamina propria (LP) lymphokine secretion profiles in inflammatory bowel disease," Journal of Immunology, 1996, 157(3): 1261-70.
GlaxoSmithKline, "Purinethol® (mercaptopurine) Prescribing Information," http://us.gsk.com/products/assets/us_purinethol.pdf. (2002).

(56) References Cited

OTHER PUBLICATIONS

Guyatt, G., et al., "A new measure of health status for clinical trials in inflammatory bowel disease," Gastroenterology, 96: 804-810 (1989).
Kim, et al., "Optimum Duration of Treatment With 6-Mercaptopurine for Crohn's Disease," American Journal of Gastroenterology, 94: 3254-3257 (1999).
Mary, J.Y., et al., "Development and validation of an endoscopic index of the severity for Crohn's disease: a prospective multicentre study," Groupe d'Etudes Therapeutiques des Affections Inflammatoires du Tube Digestif (GETAID), Gut, 30(7): 983-989 (1989).
Physician's Desk Reference 57th Edition, 2003, pp. 1615-1618.
Remington Book of Pharmacy 17th Edition, pp. 1605-1615 (1986).
Takeichi et al., "Improvement of Aqueous Solubility and Rectal Absorption of 6-Mercaptopurine by Addition of Sodium Benzoate," Bio. Pharm. Bull. 17(10): 1391-1394 (1994).
"View of NCT00287170 on Feb. 3, 2006; Pilot, Open-Label, Randomized, Parallel Group Study to Evaluate Clinical/ and Immunological Efficacy/Safety of Locally Delivered 6-MP or Calcitriol vs. Purinethol in Non-Steroid Dependent Patients with Active CD," ClinicalTrials.gov Archive, http://clinicaltrials.gov/archive/NCT0287170/2006_02_03 (Aug. 2006).
Zins, B.J., et al., "A Dose-Ranging Study of Azathioprine Pharmacokinetics After Single-Dose Administration of a Delayed-Release Oral Formulation," Journal of Clinical Pharmacology, 37(1): 38-46 (1997).
Israeli et al., "Oral Administration of Non-Absorbable Delayed Release 6-Mercaptopurine Is Locally Active in the Gut, Exerts a Systemic Immune Effect and Alleviates Crohn's Disease With Low Rate of Side Effects: Results of Double Blind Phase II Clinical Trial", Abstract, first accessed Apr. 29, 2014.
Bernstein et al., "Low Dose 6-Mercaptopurine in Inflammatory Bowel Disease is Associated with Minimal Hematologic Toxicity", Digestive Diseases and Sciences, 39(8):1638-1641 (1994).
Hanauer et al., "Postoperative Maintenance of Crohn's Disease Remission with 6-Mercaptopurine, Mesalamine, or Placebo: A 2-Year Trial" Gastroenterology 127:723-729 (2004).
Newton, Stomach Acid, Jul. 23, 2001, Department of Energy, pp. 1-2, http://replay.waybackmachine.org/20010723001702/newton.dep.anl.gov/askasci/zoo00/zoo00114.htm.
Present et al., "Treatment of Crohn's Disease with 6-Mercaptopurine" The New England Journal of Medicine 302(18):981-988 (1980).
Sandborn, WJ "Rational Dosing of Azathioprine and 6-mercaptopurine", Gut 48:591-592 (2001).
Official Action dated Aug. 4, 2014 in connection with Canadian Patent Application No. 2,271,728.
Feb. 4, 2015 Response to Official Action dated Aug. 4, 2014 in connection with Canadian Patent Application No. 2,271,728.
Jan. 4, 2012 Amendment in response to Communication issued Mar. 11, 2011 in connection with European Patent Application No. 09005528.6.
May 18, 2012 Summons to Attend Oral Proceedings in connection with European Patent Application No. 09005528.6.
Newton, Stomach Acid, Jul. 23, 2001, Department of Energy, pp. 1-2, http://replay.waybackmachine.org/2001 0723001 702/newton.dep.anl.gov/askasci/zoo00/zoo00114.htm.
Sandborn, WJ "Rational Dosing of Azathioprine and 6-mercaptopurine", Gut 48: 591-592 (2001).

\* cited by examiner

FORMULATIONS OF 6-MERCAPTOPURINE

CROSS-REFERENCE TO RELATED APPLICATIONS

This application is a continuation of U.S. Ser. No. 13/455,932, filed Apr. 25, 2012, now allowed, which is a divisional of U.S. Ser. No. 11/097,874, filed Apr. 1, 2005, now U.S. Pat. No. 8,188,067, issued May 29, 2012, which claims the benefit of provisional application Ser. No. 60/558,447, filed Apr. 1, 2004, the content of each of which is incorporated herein by reference in its entirety into this application.

FIELD OF THE INVENTION

The present invention relates to a process for preparing improved formulations of 6-mercaptopurine as well as pharmaceutical compositions comprising the improved formulations of 6-mercaptopurine where the improved formulations exhibit a faster release of 6-mercaptopurine under aqueous conditions than prior art formulations and exhibit more favorable bioavailability profiles than prior art formulations.

BACKGROUND OF THE INVENTION 6-mercaptopurine (6-MP) is a synthetic analogue of natural purine bases. After absorption into the body, it is transformed into nucleotides which interfere with nucleic acid biosynthesis, especially in the active S phase. As such, it used to slow the growth of cancerous cells. 6-MP is indicated as a monotherapy and as part of combination therapies for treating acute lymphocytic leukemia in both adults and children (Physician's Desk Reference 57$^{th}$ Edition, 2003, page 1615-1618). 6-MP also exhibits immunosuppressive properties. While it is not officially indicated for diseases where treatment with immunosuppressive agents is beneficial, 6-MP has been widely used for several such conditions, especially for Crohn's disease and colitis.

6-MP is administered orally and has partial and variable absorption and bioavailability. Approximately 50% of an oral dose is absorbed. 6-MP is further subject to metabolism, especially by thiopurine methyltransferase.

The need for improving the therapeutic potential of 6-MP has been known for a long time. U.S. Pat. Nos. 4,443,435 and 5,120,740, among others, describe the preparation of pro-drugs for 6-MP as ways of improving the use of this potent drug. Work of this sort continues, as is seen in U.S. Patent Application Publications 20040013728, 20030232760, and 20020013287. U.S. Pat. Nos. 6,680,302; 6,576,438; and 6,355,623 describe methods of improving the therapeutic outcome of 6-MP treatment in leukemia and in bowel diseases such as Crohn's disease or colitis by monitoring metabolites of the 6-MP and/or thiopurine methyltransferase activity and setting dosing based on the results. U.S. Pat. Nos. 6,692,771 and 6,680,068 and U.S. Patent Application Publications 20030077306 and 20020160049 describe emulsion formulations that may help the penetration of 6-MP into the body, while U.S. Pat. Nos. 6,602,521 and 6,372,254, and U.S. Patent Application Publications 20030133976 and 20020164371 describe drug delivery systems that might improve the therapeutics of 6-MP. None of these latter patents show data demonstrating improved bioavailability or therapeutic outcomes with 6-MP. The need still exists for formulations for improved delivery of 6-MP that improve the bioavailability thereof.

Standard 6-MP tablets (described in Physician's Desk Reference 57$^{th}$ Edition, 2003, page 1615-1618) reach full dissolution after about an hour under acidic dissolution conditions using a USP type II dissolution unit with paddles rotating at 50 rpm. 50% dissolution is reached at between 10 and 15 minutes. This rate of dissolution is not as fast as would be desirable. One method of improving the rate of dissolution of poorly soluble powders is to micronize them. In the case of 6-MP, micronization does little to improve the rate of dissolution of formulated tablets when compared to the standard formulation. The lack of improved rate of dissolution makes such tablets unlikely to show improved bioavailability when compared to the standard formulation. Further improvements to the formulation are clearly needed.

SUMMARY OF INVENTION

The present invention is directed to compositions of 6-mercaptopurine which give improved rates of dissolution when tested in a dissolution bath. It has been found that by granulating solutions of 6-mercaptopurine and pharmaceutical carriers, and forming tablets therefrom, compositions are produced that improve the rate of dissolution of the 6-mercaptopurine. It has been further found that improvement in the rate of dissolution of the 6-mercaptopurine leads to an improvement in the bioavailability of the 6-mercaptopurine.

In one embodiment, the invention relates to a pharmaceutical composition comprising 6-mercaptopurine wherein the dissolution of the 6-mercaptopurine is greater than 50% within seven minutes when the dissolution of a tablet comprising 50 mg of 6-mercaptopurine is measured in 900 ml of 0.1N HCl at 37° C. in a USP type II device using paddles rotating at 50 rpm.

In another embodiment, the invention relates to a pharmaceutical composition comprising 6-mercaptopurine wherein the time to reach 50% dissolution of the 6-mercaptopurine is reduced by at least about 30% compared to the standard formulation when the dissolution of a tablet comprising the pharmaceutical composition comprising 6-mercaptopurine is measured in 900 ml of 0.1N HCl at 37° C. in a USP type II device using paddles rotating at 50 rpm.

In another embodiment, the invention relates to a pharmaceutical composition comprising 6-mercaptopurine wherein the bioavailability is improved by at least about 15% when dosed to a mammal as compared to the standard formulation.

In another embodiment, the invention relates to a pharmaceutical composition comprising 6-mercaptopurine and a potassium, sodium, magnesium, ammonium, or calcium salt of a pharmaceutically acceptable acid.

In another embodiment, the invention relates to a pharmaceutical composition comprising 6-mercaptopurine and a potassium, sodium, magnesium, ammonium, or calcium salt of a pharmaceutically acceptable acid wherein the composition exhibits enhanced solubility in aqueous acid as compared to the standard formulation. In one embodiment, the pharmaceutically acceptable acid selected from the group consisting of acetic acid, ascorbic acid, benzoic acid, citric acid, and tartaric acid.

In another embodiment, the invention relates to a pharmaceutical composition comprising 6-mercaptopurine and potassium citrate.

In another embodiment, the invention relates to a pharmaceutical composition comprising 6-mercaptopurine wherein the 6-mercaptopurine was spray granulated from a solution onto an acceptable pharmaceutical carrier powder.

In another embodiment, the invention relates to a pharmaceutical composition comprising 6-mercaptopurine wherein the 6-mercaptopurine was spray granulated from a solution onto an acceptable pharmaceutical carrier powder wherein the spray granulation was carried out in a fluidized bed.

In another embodiment, the invention relates to a pharmaceutical composition comprising 6-mercaptopurine wherein the 6-mercaptopurine was spray granulated from a solution onto an acceptable pharmaceutical carrier powder wherein the solvent for the solution of 6-mercaptopurine comprises a solvent selected from the group consisting of dimethylformamide, dimethylacetamide, dimethylsulfoxide, and mixtures thereof.

In another embodiment, the invention relates to a pharmaceutical composition comprising 6-mercaptopurine wherein the 6-mercaptopurine was spray granulated from a solution onto an acceptable pharmaceutical carrier powder wherein the solvent for the solution of 6-mercaptopurine comprises a solvent selected from the group consisting of water and an at least about stoichiometric amount of a pharmaceutically acceptable base, ethanol and an at least about stoichiometric amount of a pharmaceutically acceptable base, and ethanol/water mixtures and an at least about stoichiometric amount of a pharmaceutically acceptable base.

In another embodiment, the invention relates to a pharmaceutical composition comprising 6-mercaptopurine wherein the 6-mercaptopurine was spray granulated from a solution onto an acceptable pharmaceutical carrier powder wherein the solvent for the solution of 6-mercaptopurine comprises a solvent selected from the group consisting of ethanol/water/potassium hydroxide, ethanol/water/sodium hydroxide, and ethanol/potassium hydroxide.

In another embodiment, the invention relates to a pharmaceutical composition comprising 6-mercaptopurine wherein the 6-mercaptopurine was spray granulated from a solution onto an acceptable pharmaceutical carrier powder wherein the solvent for the solution of 6-mercaptopurine comprises ethanol/potassium hydroxide or ethanol/water/potassium hydroxide.

In another embodiment, the invention relates to a pharmaceutical composition comprising 6-mercaptopurine wherein the 6-mercaptopurine was spray granulated from a solution onto an acceptable pharmaceutical carrier powder wherein the pharmaceutical carrier powder comprises a powder selected from the group consisting of lactose, starch, microcrystalline cellulose, calcium phosphate, powdered cellulose, sorbitol, and sucrose.

In another embodiment, the invention relates to a pharmaceutical composition comprising 6-mercaptopurine wherein the 6-mercaptopurine was spray granulated from a solution onto a pharmaceutical carrier powder that comprises lactose or microcrystalline cellulose.

In another embodiment, the invention relates to a pharmaceutical composition comprising 6-mercaptopurine wherein the 6-mercaptopurine was spray granulated from a solution onto an acceptable pharmaceutical carrier powder wherein the pharmaceutical carrier powder was pre-sprayed with a solution of a pharmaceutically acceptable acid in a molar amount that is greater than the molar amount of potassium hydroxide or other pharmaceutically acceptable base in the 6-mercaptopurine solution applied to the pharmaceutical carrier powder.

In another embodiment, the invention relates to a pharmaceutical composition comprising 6-mercaptopurine wherein the 6-mercaptopurine was spray granulated from a solution onto an acceptable pharmaceutical carrier powder wherein the pharmaceutical carrier powder was pre-sprayed with a solution comprising an acid selected from the group consisting of acetic acid, ascorbic acid, benzoic acid, citric acid, and tartaric acid.

In another embodiment, the invention relates to a pharmaceutical composition comprising 6-mercaptopurine wherein the 6-mercaptopurine was spray granulated from a solution onto an acceptable pharmaceutical carrier powder wherein the pharmaceutical carrier powder was pre-sprayed with a solution of citric acid.

In another embodiment, the invention relates to a pharmaceutical composition comprising about 3% to about 20% of 6-mercaptopurine and about 4% to about 30% of potassium citrate.

In another embodiment, the invention relates to a pharmaceutical composition comprising about 8% 6-mercaptopurine and about 5% potassium citrate.

In another embodiment, the invention relates to a pharmaceutical composition comprising about 3% to about 20% of 6-mercaptopurine wherein the 6-mercaptopurine was spray granulated from solution onto an acceptable pharmaceutical carrier powder wherein the pharmaceutical carrier powder was pre-sprayed with a solution of citric acid.

In another aspect of the invention, the invention relates to a method of making a pharmaceutical composition of 6-mercaptopurine comprising the spray granulation of a solution of 6-mercaptopurine onto a pharmaceutical carrier.

In another embodiment, the invention relates to a method of making a pharmaceutical composition of 6-mercaptopurine comprising the spray granulation of a solution of 6-mercaptopurine onto a pharmaceutical carrier wherein the 6-mercaptopurine is dissolved in a solvent that comprises a solvent selected from the group consisting of dimethylformamide, dimethylacetamide, dimethylsulfoxide, and mixtures thereof.

In another embodiment, the invention relates to a method of making a pharmaceutical composition of 6-mercaptopurine comprising the spray granulation of a solution of 6-mercaptopurine onto a pharmaceutical carrier wherein the 6-mercaptopurine is dissolved in a solvent that comprises a solvent selected from the group consisting of water and an at least about stoichiometric amount of a pharmaceutically acceptable base, ethanol and an at least about stoichiometric amount of a pharmaceutically acceptable base, and ethanol/water mixtures and an at least about stoichiometric amount of a pharmaceutically acceptable base.

In another embodiment, the invention relates to a method of making a pharmaceutical composition of 6-mercaptopurine comprising the spray granulation of a solution of 6-mercaptopurine onto a pharmaceutical carrier wherein the 6-mercaptopurine is dissolved in a solvent that comprises a solvent selected from the group consisting of ethanol/water/potassium hydroxide, ethanol/water/sodium hydroxide, and ethanol/potassium hydroxide. In certain embodiments, the solvent consists essentially of ethanol/water/potassium hydroxide, ethanol/water/sodium hydroxide, or ethanol/potassium hydroxide.

In another embodiment, the invention relates to a method of making a pharmaceutical composition of 6-mercaptopurine comprising the spray granulation of a solution of 6-mercaptopurine onto a pharmaceutical carrier wherein the 6-mercaptopurine is dissolved in ethanol/potassium hydroxide, or ethanol/water/potassium hydroxide.

In another embodiment, the invention relates to a method of making a pharmaceutical composition of 6-mercaptopurine comprising the spray granulation of a solution of 6-mercaptopurine onto a pharmaceutical carrier wherein the pharmaceutical carrier comprises a powder selected from the group consisting of lactose, starch, microcrystalline cellulose, calcium phosphate, powdered cellulose, sorbitol, and sucrose.

In another embodiment, the invention relates to a method of making a pharmaceutical composition of 6-mercaptopurine comprising the spray granulation of a solution of 6-mercaptopurine onto a pharmaceutical carrier comprising lactose powder or microcrystalline cellulose.

In another embodiment, the invention relates to a method of making a pharmaceutical composition of 6-mercaptopurine comprising the spray granulation of a solution of 6-mercaptopurine onto a pharmaceutical carrier wherein the pharmaceutical carrier was pre-sprayed with a solution of a pharmaceutically acceptable acid in a molar amount that is greater than the molar amount of potassium hydroxide or other pharmaceutically acceptable base in the 6-mercaptopurine solution applied to the pharmaceutical carrier.

In another embodiment, the invention relates to a method of making a pharmaceutical composition of 6-mercaptopurine comprising the spray granulation of a solution of 6-mercaptopurine onto a pharmaceutical carrier using a fluidized bed granulator.

In another embodiment, the invention relates to a method of spray granulating a solution of 6-mercaptopurine onto a pharmaceutical carrier to make a formulation of 6-mercaptopurine having enhanced solubility properties such that the 6-mercaptopurine dissolves in 0.1N HCl to an extent of greater than 50% within seven minutes. In another embodiment, the invention relates to a method of spray granulating a solution of 6-mercaptopurine onto a pharmaceutical carrier to make a formulation of 6-mercaptopurine having enhanced solubility properties such that the time to reach 50% dissolution of the 6-mercaptopurine formulation is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm.

In another embodiment, the invention relates to a method of spray granulating a solution of 6-mercaptopurine onto a pharmaceutical carrier to make a formulation of 6-mercaptopurine having enhanced solubility properties such that the 6-mercaptopurine dissolves in 0.1N HCl to an extent of greater than 50% within seven minutes, wherein the method comprises dissolving 6-mercaptopurine in a solvent that comprises a solvent selected from the group consisting of dimethylformamide, dimethylacetamide, dimethylsulfoxide, and mixtures thereof. In certain embodiments, the solvent consists essentially of dimethylformamide, dimethylacetamide, dimethylsulfoxide, or mixtures thereof. In another embodiment, the invention relates to a method of spray granulating a solution of 6-mercaptopurine onto a pharmaceutical carrier to make a formulation of 6-mercaptopurine having enhanced solubility properties such that the time to reach 50% dissolution of the 6-mercaptopurine formulation is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm, wherein the method comprises dissolving 6-mercaptopurine in a solvent that comprises a solvent selected from the group consisting of dimethylformamide, dimethylacetamide, dimethylsulfoxide, and mixtures thereof. In certain embodiments, the solvent consists essentially of dimethylformamide, dimethylacetamide, dimethylsulfoxide, or mixtures thereof.

In another embodiment, the invention relates to a method of spray granulating a solution of 6-mercaptopurine onto a pharmaceutical carrier to make a formulation of 6-mercaptopurine having enhanced solubility properties such that the 6-mercaptopurine dissolves in 0.1N HCl to an extent of greater than 50% within seven minutes, wherein the method comprises dissolving 6-mercaptopurine in a solvent that comprises a solvent selected from the group consisting of water and an at least about stoichiometric amount of a pharmaceutically acceptable base, ethanol and an at least about stoichiometric amount of a pharmaceutically acceptable base, and ethanol/water mixtures and an at least about stoichiometric amount of a pharmaceutically acceptable base. In another embodiment, the invention relates to a method of spray granulating a solution of 6-mercaptopurine onto a pharmaceutical carrier to make a formulation of 6-mercaptopurine having enhanced solubility properties such that the time to reach 50% dissolution of the 6-mercaptopurine formulation is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm, wherein the method comprises dissolving 6-mercaptopurine in a solvent that comprises a solvent selected from the group consisting of water and an at least about stoichiometric amount of a pharmaceutically acceptable base, ethanol and an at least about stoichiometric amount of a pharmaceutically acceptable base, and ethanol/water mixtures and an at least about stoichiometric amount of a pharmaceutically acceptable base. In certain embodiments, the solvent consists essentially of water and an at least about stoichiometric amount of a pharmaceutically acceptable base, ethanol and an at least about stoichiometric amount of a pharmaceutically acceptable base, or ethanol/water mixtures and an at least about stoichiometric amount of a pharmaceutically acceptable base.

In another embodiment, the invention relates to a method of spray granulating a solution of 6-mercaptopurine onto a pharmaceutical carrier to make a formulation of 6-mercaptopurine having enhanced solubility properties such that the 6-mercaptopurine dissolves in 0.1N HCl to an extent of greater than 50% within seven minutes, wherein the method comprises dissolving 6-mercaptopurine in a solvent that comprises a solvent selected from the group consisting of ethanol/water/potassium hydroxide, ethanol/water/sodium hydroxide, and ethanol/potassium hydroxide. In another embodiment, the invention relates to a method of spray granulating a solution of 6-mercaptopurine onto a pharmaceutical carrier to make a formulation of 6-mercaptopurine having enhanced solubility properties such that the time to reach 50% dissolution of the 6-mercaptopurine formulation is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm, wherein the method comprises dissolving 6-mercaptopurine in a solvent selected from the group consisting of ethanol/water/potassium hydroxide, ethanol/water/sodium hydroxide, and ethanol/potassium hydroxide. In certain embodiments, the solvent consists essentially of ethanol/water/potassium hydroxide, ethanol/water/sodium hydroxide, or ethanol/potassium hydroxide.

In another embodiment, the invention relates to a method of spray granulating a solution of 6-mercaptopurine onto a pharmaceutical carrier to make a formulation of 6-mercaptopurine having enhanced solubility properties such that the 6-mercaptopurine dissolves in 0.1N HCl to an extent of greater than 50% within seven minutes, wherein the method comprises dissolving 6-mercaptopurine in ethanol/potassium hydroxide or ethanol/water/potassium hydroxide. In another embodiment, the invention relates to a method of spray granulating a solution of 6-mercaptopurine onto a pharmaceutical carrier to make a formulation of 6-mercaptopurine having enhanced solubility properties such that the time to reach 50% dissolution of the 6-mercaptopurine formulation is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm, wherein the method comprises dissolving 6-mercaptopurine in ethanol/potassium hydroxide or ethanol/water/potassium hydroxide.

In another embodiment, the invention relates to a method of spray granulating a solution of 6-mercaptopurine onto a pharmaceutical carrier to make a formulation of 6-mercaptopurine having enhanced solubility properties such that the 6-mercaptopurine dissolves in 0.1N HCl to an extent of greater than 50% within seven minutes, wherein the pharmaceutical carrier comprises a powder selected from the group consisting of lactose, starch, microcrystalline cellulose, calcium phosphate, powdered cellulose, sorbitol and sucrose. In another embodiment, the invention relates to a method of spray granulating a solution of 6-mercaptopurine onto a pharmaceutical carrier to make a formulation of 6-mercaptopurine having enhanced solubility properties such that the time to reach 50% dissolution of the 6-mercaptopurine formulation is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm, wherein the pharmaceutical carrier comprises a powder selected from the group consisting of lactose, starch, microcrystalline cellulose, calcium phosphate, powdered cellulose, sorbitol and sucrose.

In another embodiment, the invention relates to a method of spray granulating a solution of 6-mercaptopurine onto a pharmaceutical carrier to make a formulation of 6-mercaptopurine having enhanced solubility properties such that the 6-mercaptopurine dissolves in 0.1N HCl to an extent of greater than 50% within seven minutes, wherein the pharmaceutical carrier comprises lactose powder. In another embodiment, the invention relates to a method of spray granulating a solution of 6-mercaptopurine onto a pharmaceutical carrier to make a formulation of 6-mercaptopurine having enhanced solubility properties such that the time to reach 50% dissolution of the 6-mercaptopurine formulation is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm, wherein the pharmaceutical carrier comprises lactose powder or microcrystalline cellulose.

In another embodiment, the invention relates to a method of spray granulating a solution of 6-mercaptopurine onto a pharmaceutical carrier to make a formulation of 6-mercaptopurine having enhanced solubility properties such that the 6-mercaptopurine dissolves in 0.1N HCl to an extent of greater than 50% within seven minutes, wherein the pharmaceutical carrier was pre-sprayed with a solution of a pharmaceutically acceptable acid in a molar amount that is greater than the molar amount of potassium hydroxide or other pharmaceutically acceptable base in the 6-mercaptopurine solution applied to the pharmaceutical carrier. In another embodiment, the invention relates to a method of spray granulating a solution of 6-mercaptopurine onto a pharmaceutical carrier to make a formulation of 6-mercaptopurine having enhanced solubility properties such that the time to reach 50% dissolution of the 6-mercaptopurine formulation is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm, wherein the pharmaceutical carrier was pre-sprayed with a solution of a pharmaceutically acceptable acid in a molar amount that is greater than the molar amount of potassium hydroxide in the 6-mercaptopurine solution applied to the pharmaceutical carrier.

In another embodiment, the invention relates to a method of spray granulating a solution of 6-mercaptopurine onto a pharmaceutical carrier to make a formulation of 6-mercaptopurine having enhanced solubility properties such that the 6-mercaptopurine dissolves in 0.1N HCl to an extent of greater than 50% within seven minutes, wherein the spray granulating uses a fluidized bed granulator. In another embodiment, the invention relates to a method of spray granulating a solution of 6-mercaptopurine onto a pharmaceutical carrier to make a formulation of 6-mercaptopurine having enhanced solubility properties such that the time to reach 50% dissolution of the 6-mercaptopurine formulation is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm, wherein the spray granulating uses a fluidized bed granulator.

In another aspect of the invention, the invention relates to a method of making a pharmaceutical composition of 6-mercaptopurine having enhanced bioavailability properties such that when dosing said composition to a mammal the bioavailability is improved by at least about 15%.

In another embodiment, the invention relates to a method of making a pharmaceutical composition of 6-mercaptopurine having enhanced bioavailability properties such that when dosing said composition to a mammal the bioavailability is improved by at least about 15%, the method comprising the spray granulation of a solution of 6-mercaptopurine onto a pharmaceutical carrier wherein the 6-mercaptopurine is dissolved in a solvent comprising a solvent selected from the group consisting of dimethylformamide, dimethylacetamide, dimethylsulfoxide, and mixtures thereof. In certain embodiment, the solvent consists essentially of dimethylformamide, dimethylacetamide, dimethylsulfoxide, or mixtures thereof.

In another embodiment, the invention relates to a method of making a pharmaceutical composition of 6-mercaptopurine having enhanced bioavailability properties such that when dosing said composition to a mammal the bioavailability is improved by at least about 15%, the method comprising the spray granulation of a solution of 6-mercaptopurine onto a pharmaceutical carrier wherein the 6-mercaptopurine is dissolved in a solvent comprising a solvent selected from the group consisting of water and an at least about stoichiometric amount of a pharmaceutically acceptable base, ethanol and an at least about stoichiometric amount of a pharmaceutically acceptable base, and ethanol/water mixtures and an at least about stoichiometric amount of a pharmaceutically acceptable base. In certain embodiments, the solvent consists essentially of water and an at least about stoichiometric amount of a pharmaceutically acceptable base, ethanol and an at least about stoichiometric amount of a pharmaceutically acceptable base, or ethanol/water mixtures and an at least about stoichiometric amount of a pharmaceutically acceptable base.

In another embodiment, the invention relates to a method of making a pharmaceutical composition of 6-mercaptopurine having enhanced bioavailability properties such that when dosing said composition to a mammal the bioavailability is improved by at least about 15%, the method comprising the spray granulation of a solution of 6-mercaptopurine onto a pharmaceutical carrier wherein the solution is 6-mercaptopurine dissolved in a solvent comprising a solvent selected from the group consisting of ethanol/water/potassium hydroxide, ethanol/water/sodium hydroxide, and ethanol/potassium hydroxide.

In another embodiment, the invention relates to a method of making a pharmaceutical composition of 6-mercaptopurine having enhanced bioavailability properties such that when dosing said composition to a mammal the bioavailability is improved by at least about 15%, the method comprising the spray granulation of a solution of 6-mercaptopurine onto a pharmaceutical carrier wherein the solution is 6-mercaptopurine dissolved in ethanol/potassium hydroxide or ethanol/water/potassium hydroxide.

In another embodiment, the invention relates to a method of making a pharmaceutical composition of 6-mercaptopurine having enhanced bioavailability properties such that when dosing said composition to a mammal the bioavailability is improved by at least about 15%, the method comprising the spray granulation of a solution of 6-mercaptopurine onto a pharmaceutical carrier wherein the pharmaceutical carrier comprises a powder selected from the group consisting of lactose, starch, microcrystalline cellulose, calcium phosphate, powdered cellulose, sorbitol, and sucrose.

In another embodiment, the invention relates to a method of making a pharmaceutical composition of 6-mercaptopurine having enhanced bioavailability properties such that when dosing said composition to a mammal the bioavailability is improved by at least about 15%, comprising the spray granulation of a solution of 6-mercaptopurine onto a pharmaceutical carrier comprising lactose.

In another embodiment, the invention relates to a method of making a pharmaceutical composition of 6-mercaptopurine having enhanced bioavailability properties such that when dosing said composition to a mammal the bioavailability is improved by at least about 15%, the method comprising the spray granulation of a solution of 6-mercaptopurine onto a pharmaceutical carrier wherein the pharmaceutical carrier was pre-sprayed with a solution of a pharmaceutically acceptable acid in a molar amount that is greater than the molar amount of potassium hydroxide or other pharmaceutically acceptable base in the 6-mercaptopurine solution applied to the pharmaceutical carrier.

In another embodiment, the invention relates to a method of making a pharmaceutical composition comprising 6-mercaptopurine having enhanced bioavailability properties such that when dosing said composition to a mammal the bioavailability is improved by at least about 15% compared to the standard formulation, the method comprising the spray granulation of a solution of 6-mercaptopurine onto a pharmaceutical carrier using a fluidized bed granulator.

In another aspect, the invention relates to a method of dosing a pharmaceutical composition comprising 6-mercaptopurine to patients in need of said drug wherein the composition displays enhanced solubility in aqueous acid compared to the standard formulation.

In another embodiment, the invention relates to a method of dosing a pharmaceutical composition comprising 6-mercaptopurine to patients in need of said drug wherein the composition displays enhanced solubility in aqueous acid such that the 6-mercaptopurine dissolves in 0.1N HCl to an extent of greater than 50% within seven minutes or wherein the time to reach 50% dissolution of the 6-mercaptopurine is reduced by at least about 30% compared to the standard formulation when the dissolution of a tablet comprising 50 mg of 6-mercaptopurine is measured in 900 ml of 0.1N HCl at 37° C. in a USP type II device using paddles rotating at 50 rpm.

In another embodiment, the invention relates to a method of dosing a pharmaceutical composition comprising 6-mercaptopurine to patients in need of said drug wherein the bioavailability is improved by at least about 15% when dosing to a mammal as compared to the standard formulation.

In another embodiment, the invention relates to a method of dosing a pharmaceutical composition comprising 6-mercaptopurine to patients in need of said drug to treat leukemia or other cancers wherein the composition displays enhanced solubility in aqueous acid as compared to the standard formulation.

In another embodiment, the invention relates to a method of dosing a pharmaceutical composition comprising 6-mercaptopurine to patients in need of said drug to treat Crohn's disease, arthritis, or colitis wherein the composition displays enhanced solubility in aqueous acid as compared to the standard formulation.

In another embodiment, the invention relates to a method of dosing a pharmaceutical composition comprising 6-mercaptopurine to patients in need of said drug to treat leukemia or other cancers wherein the bioavailability is improved by at least about 15% when dosing to a mammal as compared to the standard formulation.

In another embodiment, the invention relates to a method of dosing a pharmaceutical composition comprising 6-mercaptopurine to patients in need of said drug to treat Crohn's disease, arthritis, or colitis wherein the bioavailability is improved by at least about 15% when dosing to a mammal as compared to the standard formulation.

In another embodiment, the invention relates to a method of dosing a pharmaceutical composition comprising 6-mercaptopurine to patients in need of said drug to treat leukemia or other cancers wherein the dose administered is reduced by at least about 15% and achieves the same bioavailability as the standard formulation.

In another embodiment, the invention relates to a method of dosing a pharmaceutical composition comprising 6-mercaptopurine to patients in need of said drug to treat Crohn's disease, arthritis, or colitis wherein the dose administered is reduced by at least about 15% and achieves the same bioavailability as the standard formulation.

DESCRIPTION OF THE PREFERRED EMBODIMENTS

Figure 1:
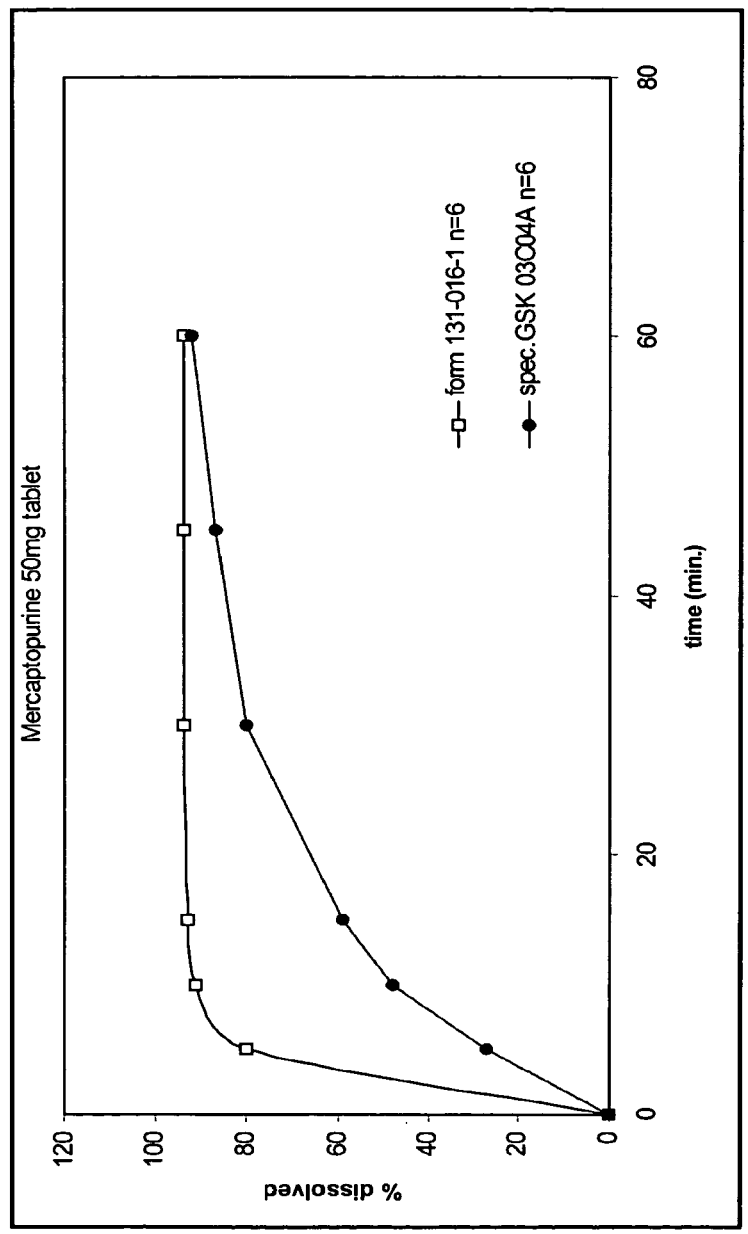
FIG. 1 shows the dissolution of a 6-mercaptopurine composition of the present invention (6-MP-IB) versus PURINETHOL® in 0.1 N HCl (sec Example 1).

The present invention is directed to compositions of 6-mercaptopurine which give improved rate of dissolution when tested in a dissolution bath and show improved bioavailability characteristics when dosed to mammals.

As used herein, the "standard formulation" is the formulation described in the Physician's Desk Reference, 57$^{th}$ edition, 2003, pages 1615-1618 and sold in the United States under the brand name PURINETHOL®.

As used herein, the term "enhanced solubility properties" or "enhanced solubility" of a material or composition of the present invention means an improved rate of dissolution of the material or composition of the present invention or an improved extent of dissolution of the material or composition of the present invention as compared to the standard formulation.

As used herein, the term "improved bioavailability" refers to the increase in concentration of a drug in the body fluid provided by the compositions of the present invention as compared to the concentration of the drug in the body fluid from the standard formulation under identical conditions. Drug bioavailability is proportional to, and is typically measured by, the total area under the curve (AUC) of the concentration of the drug found in blood or plasma versus time when measured in a pharmacokinetic trial in a human or an animal. The AUC may be expressed as AUCt, i.e. the area under the curve to the last measured time point, or AUC$_I$, i.e. the area under the curve extrapolated to infinite time. The improvement in bioavailability is measured by the percent increase in the average AUC of the subjects in the trial when dosing the improved formulation as compared to the average AUC of the same subjects obtained by dosing of the standard formulation of the drug. Alternatively, the AUC ratio of the test formulation (AUCf) to the AUC of the reference formulation (AUCr) may be calculated on a per subject basis and then averaged. A percent of the average ratio (AUCf/AUCr) above 100% is then the improvement in bioavailability.

As used herein, the term "slight stoichiometric excess" refers to a stoichiometric excess of about 0.1% to about 30%, preferably about 0.5% to about 15%, more preferably about 1% to about 5%, in terms of mole percent.

As used herein, "pre-sprayed" refers to spraying the pharmaceutical carrier powder with the acid before the acid-sprayed pharmaceutical carrier is contacted with the solution of 6-mercaptopurine.

As used herein, "powder" in reference to a pharmaceutical carrier refers to particles of the pharmaceutical carrier having a size range of 1 to 800 microns, more preferably 2 to 500 microns, and most preferably 2 to 100 microns or 50 to 400 microns, depending on the material.

One embodiment of the invention is directed to 6-MP formulations that comprise 6-MP formulated into granulates by first dissolving the 6-MP in an organic solvent. Examples of solvents that can be used to dissolve the 6-MP to an extent sufficient to be able to apply the solution to a pharmaceutical powder for further processing are dimethylformamide, dimethylacetamide, and dimethylsulfoxide, or mixtures thereof. Lactose, starch, microcrystalline cellulose, calcium phosphate, powdered cellulose, sorbitol or sucrose are examples of pharmaceutically acceptable powders that can be used as powders for this granulation. Other pharmaceutical excipient powders are known in the art and may also be used. In a more preferred embodiment the organic solvent solution of 6-MP is spray granulated on to the powder so as to form a uniform coating. A preferred method of performing this spray granulation is by using a fluidized bed granulator. A more preferred embodiment uses lactose as the pharmaceutical powder upon which the 6-MP is granulated, and a yet more preferred embodiment uses dimethylformamide to form the granulation solution. In a more preferred embodiment of the invention a lactose granulate is formed that comprises, on a weight/weight (w/w) basis, 1 to 35% 6-MP, more preferably 5 to 20% 6-MP, and most preferably about 13% 6-MP. These granulates are then mixed with other tablet excipients and formed into tablets comprising 0.5 mg to 150 mg of 6-MP for an approximate tablet weight of 500 mg with an about 50 mg dose the most preferred. Alternately the dose of 6-MP can be controlled by changing tablet weight using any of the preferred, more preferred, or most preferred granulates.

Tablets that comprise these formulations of 6-MP have improved dissolution properties. When testing these tablets in 900 ml of 0.1N HCl at 37° C. in a USP apparatus II dissolution tester with paddles rotating at 50 rpm, the rate of dissolution is greatly enhanced compared to the standard formulation. The time to 50% of dissolution is below seven minutes more preferably below five minutes and exhibits a more than 30% reduction in the time to 50% dissolution, more preferably a more than 50% reduction in time to 50% dissolution, when compared to the standard formulation.

A more preferred embodiment of this invention is directed to 6-MP formulations that comprise 6-MP formulated into granulates by first dissolving the 6-MP in ethanol containing at least about a stoichiometric amount of base, water containing at least about a stoichiometric amount of base, or mixtures of ethanol/water containing at least about a stoichiometric amount of base. The base may be selected from any pharmaceutically acceptable base such as the hydroxide or carbonate salts of potassium, sodium, magnesium, ammonium, or calcium, with potassium hydroxide being preferred. Optionally, a binder such as polyvinylpyrrolidone (PVP) may be added to the solution. This basic solution of 6-MP is granulated onto a pharmaceutical carrier selected from the group of lactose, starch, microcrystalline cellulose, calcium phosphate, powdered cellulose, sorbitol, or sucrose. Other pharmaceutical excipient powders are known in the art and may also be used. In a preferred embodiment, the basic solvent solution of 6-MP is spray granulated on to the powder so as to form a uniform coating. A preferred method of performing this spray granulation is by using a fluidized bed granulator. A more preferred embodiment uses lactose as the pharmaceutical powder upon which the 6-MP is granulated and a most preferred embodiment uses an ethanol/water solvent mixture and potassium hydroxide as the base. In another more preferred embodiment, microcrystalline cellulose is used as the pharmaceutical powder upon which the 6-MP is granulated, and a most preferred embodiment uses an ethanol/water solvent mixture and potassium hydroxide as the base. The basic granulate is neutralized with a slight stoichiometric excess of any pharmaceutically acceptable acid. Examples of such acids are acetic acid, ascorbic acid, benzoic acid, citric acid, and tartaric acid. In a more preferred embodiment the acid selected is citric acid. In a more preferred embodiment, the pharmaceutically acceptable acid is precoated in a slight stoichiometric excess onto the pharmaceutically acceptable carrier before it is used in the granulation with the basic organic solution of 6-MP. In a more preferred embodiment, the pharmaceutically acceptable carrier is lactose and the pharmaceutically acceptable acid that is preloaded in a slight stoichiometric excess is citric acid. A more preferred mode for applying the acid is spray granulation and a most preferred method uses a fluidized bed granulator. In a preferred embodiment of the invention a lactose granulate is formed that comprises 1 to 35% 6-MP, more preferably 5 to 20% 6-MP, and most preferably about 11% 6-MP. In another preferred embodiment of the invention, a microcrystalline cellulose granulate is formed that comprises 1 to 35% 6-MP, more preferably 5 to 20% 6-MP, and most preferably about 11% 6-MP. These granulates further comprise salts of pharmaceutically acceptable acids, more preferably the sodium or potassium salts of acetic acid, ascorbic acid, benzoic acid, citric acid, or tartaric acid and most preferably the potassium salt of citric acid. The potassium citrate is present in about a stoichiometric amount compared to the 6-MP. These granulates are then mixed with other tablet excipients and formed into tablets comprising 0.5 mg to 150 mg of 6-MP for an approximate total tablet weight of 650 mg with an about 50 mg dose of 6-MP being the most preferred. Alternately the dose of 6-MP can be controlled by changing tablet weight using any of the preferred, more preferred, or most preferred granulates. In another embodiment the final dosage form comprises about 3% to about 20% of 6-mercaptopurine and about 2% to about 30% of potassium citrate and more preferably about 5% to about 15% of 6-MP and about 2% to about 20% potassium citrate, and most preferably about 8% 6-mercaptopurine and about 5% potassium citrate.

Tablets that comprise these formulations of 6-MP have improved dissolution properties. When testing these tablets in 900 ml of 0.1N HCl at 37° C. in a USP apparatus II dissolution tester with paddles rotating at 50 rpm, the rate of dissolution is greatly enhanced as compared to the standard formulation. The time to 50% of dissolution is below seven minutes, more preferably below five minutes, and exhibits a more than 30% reduction in the time to 50% dissolution, more preferably a more than 50% reduction in time to 50% dissolution, when compared to the standard formulation.

Another aspect of the invention is a method of producing compositions of 6-mercaptopurine which give improved rates of dissolution when tested in a dissolution bath. Standard formulation 6-MP tablets reach full dissolution after about an hour under acidic dissolution conditions using a USP type II dissolution unit with paddles rotating at 50 rpm. 50% dissolution is reached at between 10 and 15 minutes. Improved rates of dissolution are defined herein as a time to 50% of dissolution less than or equal to about seven minutes, more preferably less than or equal to about five minutes, or a more than 30% reduction in the time to 50% dissolution, more preferably a more than or equal to 50% reduction in the time to 50% dissolution, compared to the standard formulation.

One aspect of the present invention is a method of forming 6-MP formulations that comprises granulating 6-MP into granulates by first dissolving the 6-MP in an organic solvent. Examples of solvents that can be used to dissolve the 6-MP to an extent sufficient to be able to apply the solution to a pharmaceutical powder for further processing are dimethylformamide, dimethylacetamide, and dimethylsulfoxide, or mixtures thereof. Lactose, starch, microcrystalline cellulose, calcium phosphate, powdered cellulose, sorbitol, or sucrose are examples of pharmaceutically acceptable powders that can be used as powders for this granulation. Other pharmaceutical excipient powders are known in the art and may also be used. In a more preferred embodiment the organic solvent solution of 6-MP is spray granulated on to the powder so as to form a uniform coating. A preferred method of performing this spray granulation is by using a fluidized bed granulator. A more preferred embodiment uses lactose as the pharmaceutical powder upon which the 6-MP is granulated and a yet more preferred embodiment uses dimethylformamide to form the granulation solution. In a more preferred embodiment of the invention, a lactose granulate is formed that comprises 1 to 35% 6-MP, more preferably 5 to 20% 6-MP, and most preferably about 13% 6-MP.

These granulates are then mixed with other tablet excipients and formed into tablets comprising 0.5 mg to 150 mg of 6-MP for an approximate tablet weight of 500 mg with an about 50 mg dose being the most preferred. Alternatively, the dose of 6-MP can be controlled by changing tablet weight using any of the preferred, more preferred, or most preferred granulates.

Tablets that comprise formulations of 6-MP made by this method have improved dissolution properties. When testing these tablets in 900 ml of 0.1N HCl at 37° C. in a USP apparatus II dissolution tester with paddles rotating at 50 rpm, the rate of dissolution is greatly enhanced compared to the standard formulation. The time to 50% of dissolution is below seven minutes, more preferably below five minutes, and exhibits a more than 30% reduction in the time to 50% dissolution, more preferably a more than 50% reduction in time to 50% dissolution, when compared to the standard formulation.

A more preferred embodiment of this invention is a method of making 6-MP formulations that comprises granulating 6-MP into granulates by first dissolving the 6-MP in ethanol containing at least a stoichiometric amount of base, water containing at least a stoichiometric amount of base, or mixtures of ethanol/water containing at least a stoichiometric amount of base. The base may be selected from any pharmaceutically acceptable base such as the hydroxide or carbonate salts of potassium, sodium, magnesium, ammonium, or calcium, with potassium hydroxide being more preferred. Optionally, a binder such as polyvinylpyrrolidone (PVP) may be added to the solution. This basic solution of 6-MP is granulated onto a pharmaceutical carrier selected from the group consisting of lactose, starch, microcrystalline cellulose, calcium phosphate, powdered cellulose, sorbitol, and sucrose. Other pharmaceutical excipient powders are known in the art and may also be used. In a more preferred embodiment the basic solvent solution of 6-MP is spray granulated on to the powder so as to form a uniform coating. A preferred method of performing this spray granulation is by using a fluidized bed granulator. A more preferred embodiment uses lactose as the pharmaceutical powder upon which the 6-MP is granulated, and a most preferred embodiment uses an ethanol/water solvent mixture and potassium hydroxide as the base. In another more preferred embodiment, microcrystalline cellulose is used as the pharmaceutical powder upon which the 6-MP is granulated, and a most preferred embodiment uses an ethanol/water solvent mixture and potassium hydroxide as the base. The basic granulate is neutralized with a stoichiometric excess of any pharmaceutically acceptable acid. Examples of such acids are acetic acid, ascorbic acid, benzoic acid, citric acid, and tartaric acid. In a more preferred embodiment, the acid selected is citric acid. In a more preferred embodiment, the pharmaceutically acceptable acid is preloaded in a slight stoichiometric excess onto the pharmaceutically acceptable carrier before it is used in the granulation with the basic organic solution of 6-MP. In a more preferred embodiment, the pharmaceutically acceptable carrier is lactose and the pharmaceutically acceptable acid that is preloaded in a slight stoichiometric excess is citric acid. A more preferred method for applying the acid is spray granulation, and a most preferred method uses a fluidized bed granulator. In a preferred embodiment of the invention, a lactose granulate is formed that comprises 1 to 35% 6-MP, preferably 5 to 20% 6-MP, and most preferably about 11% 6-MP. In another preferred embodiment of the invention, a microcrystalline cellulose granulate is formed that comprises 1 to 35% 6-MP, more preferably 5 to 20% 6-MP, and most preferably about 11% 6-MP. These granulates further comprise salts of pharmaceutically acceptable acids, preferably the sodium or potassium salts of acetic acid, ascorbic acid, benzoic acid, citric acid, or tartaric acid, and most preferably the potassium salt of citric acid. The potassium citrate is present in about a stoichiometric amount compared to the 6-MP. These granulates are then mixed with other tablet excipients and formed into tablets comprising 0.5 mg to 150 mg of 6-MP for an approximate total tablet weight of 650 mg, with an about 50 mg dose of 6-MP in the tablet being most preferred. Alternatively, the dose of 6-MP can be controlled by changing tablet weight using any of the preferred, more preferred, or most preferred granulates. In another embodiment, the final dosage form comprises about 3% to about 20% of 6-mercaptopurine and about 2% to about 30% of potassium citrate, preferably about 5% to about 15% of 6-MP and about 2% to about 20% potassium citrate, and most preferably about 8% 6-mercaptopurine and about 5% potassium citrate.

Tablets that comprise formulations of 6-MP made by this method have improved dissolution properties. When testing these tablets in 900 ml of 0.1N HCl at 37° C. in a USP apparatus II dissolution tester with paddles rotating at 50 rpm, the rate of dissolution is greatly enhanced compared to the standard formulation. The time to 50% of dissolution is below seven minutes, preferably below five minutes, and exhibits a more than 30% reduction in the time to 50% dissolution, preferably a more than 50% reduction in time to 50% dissolution, when compared to the standard formulation.

Another aspect of the invention is a method of producing compositions of 6-mercaptopurine which provide enhanced bioavailability compared to the standard formulation. The enhanced bioavailability may be a rise in average AUCt or $AUC_I$ of about 5% or more, preferably a rise of about 15% or more, and most preferably a rise of 20% or more. Alternatively, the average ratio of the individual AUCt values for the test and reference formulations is about 1.05 or more, preferably 1.15 or more, and most preferably 1.20 or more. One embodiment of this aspect of the invention is a method of making 6-MP formulations that comprises granulating 6-MP into granulates by first dissolving the 6-MP in an organic solvent. Examples of solvents that can be used to dissolve the 6-MP to an extent sufficient to be able to apply the solution to a pharmaceutical powder for further processing are dimethylformamide, dimethylacetamide, and dimethylsulfoxide, or mixtures thereof. Lactose, starch, microcrystalline cellulose, calcium phosphate, powdered cellulose, sorbitol, or sucrose are examples of pharmaceutically acceptable powders that can be used as powders for this granulation. Other pharmaceutical excipient powders are known in the art and may also be used. In a more preferred embodiment, the organic solvent solution of 6-MP is spray granulated on to the powder so as to form a uniform coating. A preferred method of performing this spray granulation is by using a fluidized bed granulator. A more preferred embodiment uses lactose as the pharmaceutical powder upon which the 6-MP is granulated, and a yet more preferred embodiment uses dimethylformamide to form the granulation solution. In a more preferred embodiment of the invention, a lactose granulate is formed that comprises 1 to 35% 6-MP, preferably 5 to 20% 6-MP, and most preferably about 13% 6-MP. These granulates are then mixed with other tablet excipients and formed into tablets comprising 0.5 mg to 150 mg of 6-MP for an approximate total tablet weight of 500 mg, with an about 50 mg of 6-MP in that tablet being the dose most preferred. Alternatively, the dose of 6-MP can be controlled by changing tablet weight using any of the preferred, more preferred, or most preferred granulates.

A more preferred embodiment of this invention is a method of producing 6-MP formulations that comprises granulating 6-MP into granulates by first dissolving the 6-MP in ethanol containing at least about a stoichiometric amount of base, water containing at least about a stoichiometric amount of base, or mixtures of ethanol/water containing at least about a stoichiometric amount of base. The base may be selected from any pharmaceutically acceptable base such as the hydroxide or carbonate salts of potassium, sodium, magnesium, ammonium, or calcium, with potassium hydroxide being more preferred. Optionally, a binder such as polyvinylpyrrolidone (PVP) may be added to the solution. This basic solution of 6-MP is granulated onto a pharmaceutical carrier selected from the group of lactose, starch, microcrystalline cellulose, calcium phosphate, powdered cellulose, sorbitol, and sucrose. Other pharmaceutical excipient powders are known in the art and may also be used. In a more preferred embodiment the basic solvent solution of 6-MP is spray granulated on to the powder so as to form a uniform coating. A preferred method of performing this spray granulation is by using a fluidized bed granulator. A more preferred embodiment uses lactose as the pharmaceutical powder upon which the 6-MP is granulated, and a most preferred embodiment uses an ethanol/water solvent mixture and potassium hydroxide as the base. In another more preferred embodiment, microcrystalline cellulose is used as the pharmaceutical powder upon which the 6-MP is granulated, and a most preferred embodiment uses an ethanol/water solvent mixture and potassium hydroxide as the base. The basic granulate is neutralized with a slight stoichiometric excess of any pharmaceutically acceptable acid. Examples of such acids are acetic acid, ascorbic acid, benzoic acid, citric acid, and tartaric acid. In a more preferred embodiment, the acid selected is citric acid. In a more preferred embodiment, the pharmaceutically acceptable acid is preloaded in a slight stoichiometric excess onto the pharmaceutically acceptable carrier before it is used in the granulation with the basic organic solution of 6-MP. In a more preferred embodiment, the pharmaceutically acceptable carrier is lactose and the pharmaceutically acceptable acid that is preloaded in an about slight stoichiometric excess is citric acid. A more preferred mode for applying the acid is spray granulation and a most preferred method uses a fluidized bed granulator. In a preferred embodiment of the invention a lactose granulate is formed that comprises 1 to 35% 6-MP, preferably 5 to 20% 6-MP, and most preferably about 11% 6-MP. In another preferred embodiment of the invention, a microcrystalline cellulose granulate is formed that comprises 1 to 35% 6-MP, more preferably 5 to 20% 6-MP, and most preferably about 11% 6-MP. These granulates further comprise salts of pharmaceutically acceptable acids, preferably the sodium or potassium salts of acetic acid, ascorbic acid, benzoic acid, citric acid, or tartaric acid, and most preferably the potassium salt of citric acid. The potassium citrate is present in about a stoichiometric amount compared to the 6-MP. These granulates are then mixed with other tablet excipients and formed into tablets comprising 0.5 mg to 150 mg of 6-MP for an approximate total tablet weight of 650 mg, with an about 50 mg dose of 6-MP in the tablet being preferred. Alternatively, the dose of 6-MP can be controlled by changing tablet weight using any of the preferred, more preferred, or most preferred granulates. In another embodiment the final dosage form comprises about 3% to about 20% of 6-mercaptopurine and about 2% to about 30% of potassium citrate, preferably about 5% to about 15% of 6-MP and about 2% to about 20% potassium citrate, and most preferably about 8% 6-mercaptopurine and about 5% potassium citrate.

Tablets that comprise formulations of 6-MP made by this method have improved dissolution properties and improved bioavailability, by more than 5%, preferably by more than 15%, and most preferably by more than 20%, when tested in beagle dogs.

Another aspect of this invention is a method of treating patients in need of treatment with 6-MP by dosing them with formulations of 6-MP that have enhanced bioavailability compared to the standard formulation. Examples of patients in need of treatment with 6-MP are patients suffering from any disease in which a cytotoxic drug is beneficial such as leukemia, especially acute lymphocytic leukemia, or other cancers, as well as patients suffering from any disease for which an immunosuppressant drug is beneficial, such as Crohn's diseases, ulcerative colitis, or arthritis.

The enhanced bioavailability may be a rise in average AUCt or AUC$_I$ of about 5% or more, preferably a rise of about 15% or more, and most preferably a rise of about 20% or more. Alternatively, the average ratio of the individual AUCt values for the test and reference formulations is about 1.05 or more, preferably 1.15 or more, and most preferably about 1.20 or more. One embodiment of this aspect of the invention is a method of dosing, to a mammal, 6-MP formulations that comprise granulates that were produced by first dissolving the 6-MP in an organic solvent. Examples of solvents that can be used to dissolve the 6-MP to an extent sufficient to be able to apply the solution to a pharmaceutical powder for further processing are dimethylformamide, dimethylacetamide, and dimethylsulfoxide, or mixtures thereof. Lactose, starch, microcrystalline cellulose, calcium phosphate, powdered cellulose, sorbitol, or sucrose are examples of pharmaceutically acceptable powders that can be used as powders for this granulation. Other pharmaceutical excipient powders are known in the art and may also be used. In a more preferred embodiment the organic solvent solution of 6-MP is spray granulated on to the powder so as to form a uniform coating. A preferred method of performing this spray granulation is by using a fluidized bed granulator. A more preferred embodiment uses lactose as the pharmaceutical powder upon which the 6-MP is granulated and a yet more preferred embodiment uses dimethylformamide to form the granulation solution. In a more preferred embodiment of the invention a lactose granulate is formed that comprises 1 to 35% 6-MP, more preferably 5 to 20% 6-MP and most preferably about 13% 6-MP. These granulates are then mixed with other tablet excipients and formed into tablets comprising 0.5 mg to 150 mg of 6-MP for an approximate tablet weight of 500 mg with an about 50 mg dose the most preferred. Alternately the dose of 6-MP can be controlled by changing tablet weight using any of the preferred, more preferred, or most preferred granulates.

Other tablet excipients that may be used to formulate tablets comprising the pharmaceutical compositions of the present invention include binders, diluents, disintegrants, lubricants, colorants, and taste masking agents. Suitable binders include microcrystalline cellulose, modified celluloses, and povidone. Suitable diluents include calcium hydrogen phosphate (CaHPO$_4$), anhydrous; lactose; and mannitol. Suitable disintegrants include sodium starch glycollate (type A), sodium starch glycollate (type B), and crospovidone. Suitable lubricants include sodium stearyl fumarate, dimeticone, macrogol 6000, hydrogenated castor oil, and stearic acid.

A more preferred embodiment of this invention is a method of dosing, to a mammal, 6-MP formulations that comprise granulates that were produced by first dissolving the 6-MP in ethanol containing at least about a stoichiometric amount of base, water containing at least about a stoichiometric amount of base, or mixtures of ethanol/water containing at least about a stoichiometric amount of base. The base may be selected from any pharmaceutically acceptable base such as the hydroxide or carbonate salts of potassium, sodium, magnesium, ammonium, or calcium, with potassium hydroxide being preferred. Optionally, a binder such as polyvinylpyrrolidone (PVP) may be added to the solution. This basic solution of 6-MP is granulated onto a pharmaceutical carrier selected from the group of lactose, starch, microcrystalline cellulose, calcium phosphate, powdered cellulose, sorbitol and sucrose. Other pharmaceutical excipient powders are known in the art and may also be used. In a more preferred embodiment the basic solvent solution of 6-MP is spray granulated on to the powder so as to form a uniform coating. A preferred method of performing this spray granulation is by using a fluidized bed granulator. A more preferred embodiment uses lactose as the pharmaceutical powder upon which the 6-MP is granulated and a most preferred embodiment uses an ethanol/water solvent mixture and potassium hydroxide as the base. In another more preferred embodiment, microcrystalline cellulose is used as the pharmaceutical powder upon which the 6-MP is granulated, and a most preferred embodiment uses an ethanol/water solvent mixture and potassium hydroxide as the base. The basic granulate is neutralized with an about slight stoichiometric excess of any pharmaceutically acceptable acid. Examples of such acids are acetic acid, ascorbic acid, benzoic acid, citric acid, and tartaric acid. In a more preferred embodiment, the acid selected is citric acid. In a more preferred embodiment, the pharmaceutically acceptable acid is preloaded in a slight stoichiometric excess onto the pharmaceutically acceptable carrier before it is used in the granulation with the basic organic solution of 6-MP. In a more preferred embodiment the pharmaceutically acceptable carrier is lactose and the pharmaceutically acceptable acid that is preloaded in a slight stoichiometric excess is citric acid. A more preferred mode for applying the acid is spray granulation and a most preferred method uses a fluidized bed granulator. In a preferred embodiment of the invention, a lactose granulate is formed that comprises 1 to 35% 6-MP, more preferably 5 to 20% 6-MP, and most preferably about 11% 6-MP. In another preferred embodiment of the invention, a microcrystalline cellulose granulate is formed that comprises 1 to 35% 6-MP, more preferably 5 to 20% 6-MP, and most preferably about 11% 6-MP. These granulates further comprise salts of pharmaceutically acceptable acids, more preferably the sodium or potassium salts of acetic acid, ascorbic acid, benzoic acid, citric acid, or tartaric acid and most preferably the potassium salt of citric acid. The potassium citrate is present in about a stoichiometric amount compared to the 6-MP. These granulates are then mixed with other tablet excipients and formed into tablets comprising 0.5 mg to 150 mg of 6-MP for an approximate tablet weight of 650 mg, with an about 50 mg dose the most preferred. Alternatively, the dose of 6-MP can be controlled by changing tablet weight using any of the preferred, more preferred, or most preferred granulates. In another embodiment, the final dosage form comprises about 3% to about 20% of 6-mercaptopurine and about 2% to about 30% of potassium citrate and more preferably about 5% to about 15% of 6-MP and about 2% to about 20% potassium citrate, and most preferably about 8% 6-mercaptopurine and about 5% potassium citrate.

In one embodiment, the patients in need of said treatment are treated with a dose similar to the dose given with the standard formulation, thereby achieving enhanced efficacy. In another embodiment, the dose of treatment is lowered so as to have the same bioavailability as the standard treatment but achieved with a lower dose of drug. The result of the treatment is the same efficacy as the standard formulation with less exposure to potent drugs and an improved side effect profile.

Methods of making 6-mercaptopurine are known in the art. For example, 6-mercaptopurine can be made according to the processes described in G. H. Hitchings, G. B. Elion, U.S. Pat. No. 2,697,702 or G. B. Elion, et al., J. Am. Chem. Soc. 74,411 (1952).

EXAMPLES

Example 1

Mercaptopurine Spray Granulated from Dimethylformamide Solution

6-Mercaptopurine (6-MP, Orion-Fermion, 13.2 gm) was dissolved in dimethylformamide (DMF, Merck, 1.25 liter) with stirring over a period of 30 minutes. Lactose (DMV, 85 gm) was charged into a fluidized bed drier/granulator (FBD) and suspended by airflow. The air inlet temperature was 70° C. The DMF solution of 6-MP was sprayed into the suspended fluidized bed at a rate that maintained a bed temperature of 36° C. Total spraying time was 6 hours. The granulated lactose was subsequently dried in the FBD at 70° C. for one hour and sieved through a 1.0 mm screen. The dry granulate (100 gm which contained 13.2 gm 6-MP) was mixed with potato starch (AVEBE, 25.9 grams), microcrystalline cellulose (Avicel 101, FMC, 13.2 grams) and croscarmellose sodium (Ac-Di-Sol, FMC, 3.7 grams) for 8 minutes. Magnesium stearate (Brenntag, 0.5 grams) was added and the powder mixed for a further minute. The powder was pressed into tablets using a Korsch 106 rotary tablet press, using 12 mm flat faced round punches with the inscription φβ571. Final tablet weight was 542 mg and the 6-MP content was 50 mg (6-MP-IB batch 131-016-1).

Dissolution analysis was carried out in a USP type II dissolution bath (VanKel) using 900 ml of 0.1N HCl kept at 37° C. and stirred at 50 rpm. Samples were taken at 5, 10 15, 30, 45, and 60 minutes. PURINETHOL® (batch GSK03C04A) was tested under identical conditions. The 6-MP content of the samples was measured by UV spectroscopy at 325 nm against a standard curve. The results of the measurements are given in Table 1 and shown graphically in FIG. 1.

TABLE 1

Dissolution of 6-mercaptopurine from 6-MP-IB 131-016-1 vs. PURINETHOL ® in 0.1N HCl

| 6-MP-IB 131-016-1 | | PURINETHOL ® GSK03C04A | |
|---|---|---|---|
| Time (min) | Cumulative % | Time (min) | Cumulative % |
| 0 | 0 | 0 | 0 |
| 5 | 80 | 5 | 27 |
| 10 | 91 | 10 | 48 |
| 15 | 93 | 15 | 59 |
| 30 | 94 | 30 | 80 |
| 45 | 94 | 45 | 87 |
| 60 | 94 | 60 | 92 |

The results of the dissolution show that the DMF spray granulated 6-MP tablets give a much faster dissolution in 0.1N HCl than the standard formulation tablets. The time to 50% dissolution was better than halved with 80% being dissolved in 5 minutes and 91% at 10 minutes. The improved speed of dissolution of the product is expected to lead to improved bioavailability in vivo.

Example 2

Mercaptopurine Stray Granulated from Ethanol/Water/KOH Solution

Citric acid (Merck, 4.6 gm) was dissolved in 69 ml ethanol/water (70:30). This solution was sprayed onto a bed of lactose (DMV, 80 grams) suspended in an FBD granulator using the following conditions: inlet air temperature 55° C., bed temperature 28° C. 6-mercaptopurine (Orion-Fermion, 11.4 gm) was dissolved in 430 ml ethanol/water (80:20) containing pre-dissolved potassium hydroxide (Merck, 4.0 gram). The 6-MP solution was then sprayed onto the lactose/citric acid bed in the FBD using the following conditions: inlet air temperature 55° C., bed temperature 28° C. The bed was dried in situ at 55° C. for 30 minutes. The dried granulate was passed through a 1.6 mm sieve. The dried and sieved granulate (100 grams) was mixed with potato starch (AVEBE, 26 grams), microcrystalline cellulose (Avicel 101, FMC, 11.4 grams), crospovidone (ISP Global Tech, 7.5 grams), and colloidal silicon dioxide (Degussa, 0.5 grams) for 8 minutes. Magnesium stearate (Brenntag, 2.2 gram) was added and the powder mixed for a further 2 minutes. The powder was pressed into tablets using a Korsch 106 rotary tablet press using 12 mm flat faced round punches with the inscription φβ571. Final tablet weight was 647 mg and the 6-MP content was 50 mg (6-MP-IB batch 131-018-6)

Figure 2:
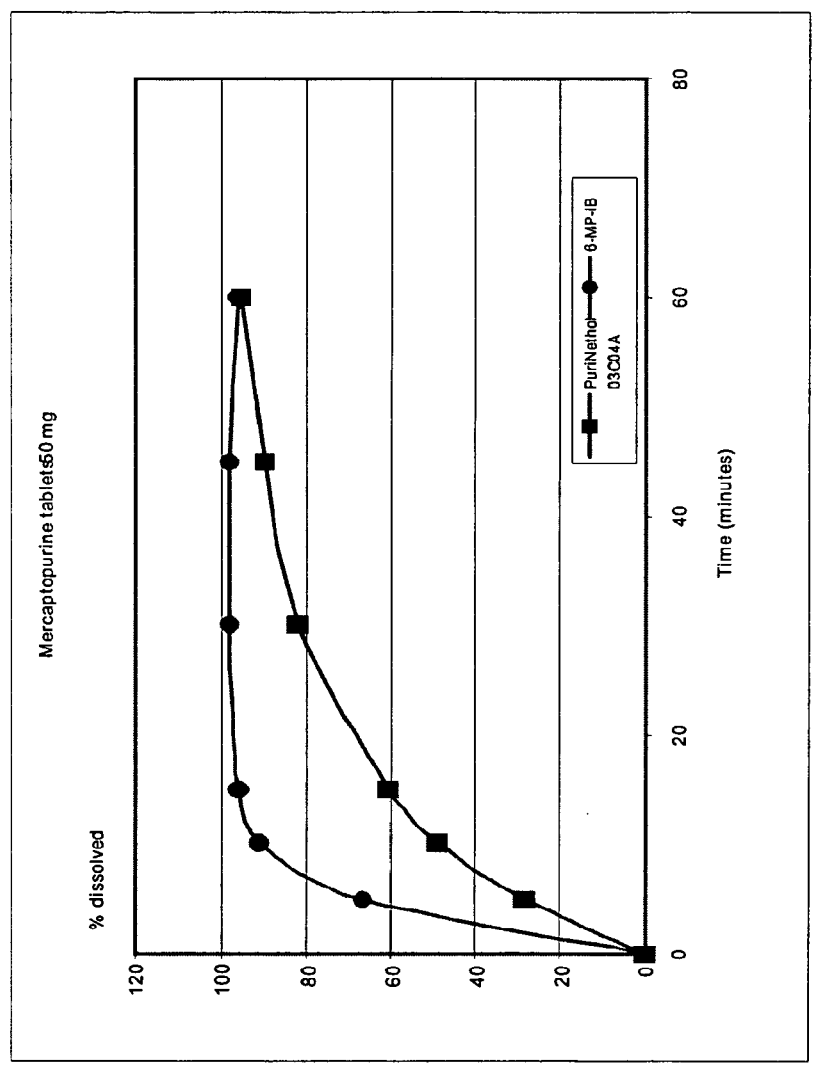
FIG. 2 shows the dissolution of a 6-mercaptopurine composition of the present invention from (6-MP-IB batch) vs. PURINETHOL® in 0.1N HCl (see Example 2).

Dissolution analysis was carried out in a USP type II dissolution bath (VanKel) using 900 ml of 0.1N HCl kept at 37° C. and stirred at 50 rpm. Samples were taken at 5, 10, 15, 30, 45, and 60 minutes. PURINETHOL® (batch GSK03CD4A) was tested under identical conditions. The 6-MP content of the samples was measured by UV spectroscopy at 325 nm against a standard curve. The results of the measurements are given in Table 2 and shown graphically in FIG. 2.

TABLE 2

Dissolution of 6-mercaptopurine from 6-MP-IB 131-018-6 vs. PURINETHOL ® on 0.1N HCl

| 6-MP-IB 131-018-6 | | PURINETHOL ® GSK03C04A | |
|---|---|---|---|
| Time (min) | Cumulative % | Time (min) | Cumulative % |
| 0 | 0 | 0 | 0 |
| 5 | 67 | 5 | 27 |
| 10 | 91 | 10 | 48 |
| 15 | 96 | 15 | 59 |
| 30 | 98 | 30 | 80 |
| 45 | 98 | 45 | 87 |
| 60 | 96 | 60 | 92 |

The results of the dissolution show that the basic ethanolic-water spray granulated 6-MP tablets give a much faster dissolution in 0.1N HCl than the standard formulation tablets. The time to 50% dissolution was better than halved with 67% being dissolved in 5 minutes and better than 90% at 10 minutes. The improved speed of dissolution of the product is expected to lead to improved bioavailability in vivo.

Example 3

Tablets of 6-MP Coated on Microcrystalline Cellulose or Lactose

This example present data from tablets in which 6-MP is coated on either microcrystalline cellulose or lactose. Table 3 shows a batch formula for tablets having 40 mg of 6-MP per tablet (the batch is for ~1000 tablets), tablet weight 523 mg using 50% ethanol by volume (44.4% by weight) in both spraying steps.

TABLE 3

|  | Raw material | (g) | (g) |
| --- | --- | --- | --- |
| 1 | Lactose monohydrate | 280 | — |
| 2 | Macrocrystalline Cellulose | — | 280 |
| 3 | Citric Acid anhydrate | 19.5 | 19.5 |
| 4 | Alcohol denatured or USP | 96[#] | 96[#] |
| 5 | Purified Water | 120 | 120 |
| 6 | Mercaptopurine | 40.0 | 40.0 |
| 7 | Potassium hydroxide | 16.2 | 16.2 |
| 8 | PVP K30 | — | 10.4 |
| 9 | Alcohol denatured or USP | 600[#] | 600[#] |
| 10 | Purified Water | 750 | 750 |
| 11 | Colloidal Silicon Dioxide | 1.6 | 1.6 |
| 12 | Potato Starch | 24.4 | 24.4 |
| 13 | Crospovidone | 26.4 | 26.4 |
| 14 | Macrocrystalline Cellulose | 91.6 | 91.6 |
| 15 | PVP K30 | 15.6 | 5.2 |
| 16 | Magnesium Stearate | 8.0 | 8.0 |

[#]Density 0.8 g/mL

Manufacturing Method

Solution A.

Mix alcohol (denatured or USP) (4) with purified water (5), add and dissolve citric acid (3).

Coating Step I (Aeromatic Strea 1)

Spray solution A on to lactose monohydrate (1) or microcrystalline cellulose (MCC) (2).

Process Parameters:

Atomizing air: 1 bar
Nozzle: 1.0 mm
Inlet temperature: 55° C.
Exhaust temperature: approx. 24° C.
Spray rate: approx. 9-10 g/min
Airflow rate: approx. 54 m³/h Solution B.

Mix alcohol (denatured or USP) (9) with purified water (10), add and dissolve potassium hydroxide (7). Add and dissolve 6-mercaptopurine (6). Optionally, PVP K30 (8) may be dissolved in this solution (either with lactose or with MCC-shown here with MCC).

Coating Step II (Aeromatic Strea 1)

Spray solution B onto the lactose monohydrate with citric acid or MCC with citric acid of coating step I.

Process Parameters:

Atomizing air: 1 bar
Nozzle: 1.0 mm
Inlet temperature: 55° C.
Exhaust temperature: approx. 24° C.
Spray rate: approx. 10-11 g/min
Airflow rate: approx. 54-80 m³/h Drying Dry the lactose/citric acid/potassium hydroxide/6-mercaptopurine mixture or the MCC/citric acid/potassium hydroxide/PVP/6-mercaptopurine mixture.

Process Parameters:

Inlet temperature: 55° C.
Exhaust temperature: approx. 34° C.
Airflow rate: approx. 54-80 m³/h Sieving I Pass the lactose/citric acid/potassium hydroxide/6-mercaptopurine mixture or the MCC/citric acid/potassium hydroxide/PVP/6-mercaptopurine mixture through a 1.0 mm sieve.

Pass colloidal silicon dioxide (11) through a 1.0 mm sieve.

Mixing 1

Blend the lactose/citric acid/potassium hydroxide/6-mercaptopurine mixture or the MCC/citric acid/potassium hydroxide/PVP/6-mercaptopurine mixture with colloidal silicon dioxide for 2 minutes in a cubic tumbler.

Sieving II

Pass potato starch (12), crospovidone (13), microcrystalline cellulose (14) and PVP K30 (15) through 1.0 mm sieve.

Mixing II

Blend the lactose/citric acid/potassium hydroxide/6-mercaptopurine/colloidal silicon dioxide mixture or the MCC/citric acid/potassium hydroxide/PVP/6-mercaptopurine/colloidal silicon dioxide mixture with potato starch, crospovidone, microcrystalline cellulose and PVP K30 for 8 minutes in a cubic tumbler.

Sieving III

Pass magnesium stearate (16) through a 1.0 mm sieve.

Mixing III

Blend the mixture of Mixing step II with magnesium stearate for 2 minutes in a cubic tumbler.

Tabletting

Compress the final mixture into tablets with tablet weight 523 mg (12 mm, round convex R=9.5). Resistance to crushing of 5-7 Kp, friability max 1.0%, disintegration time<5 min.

Figure 4:
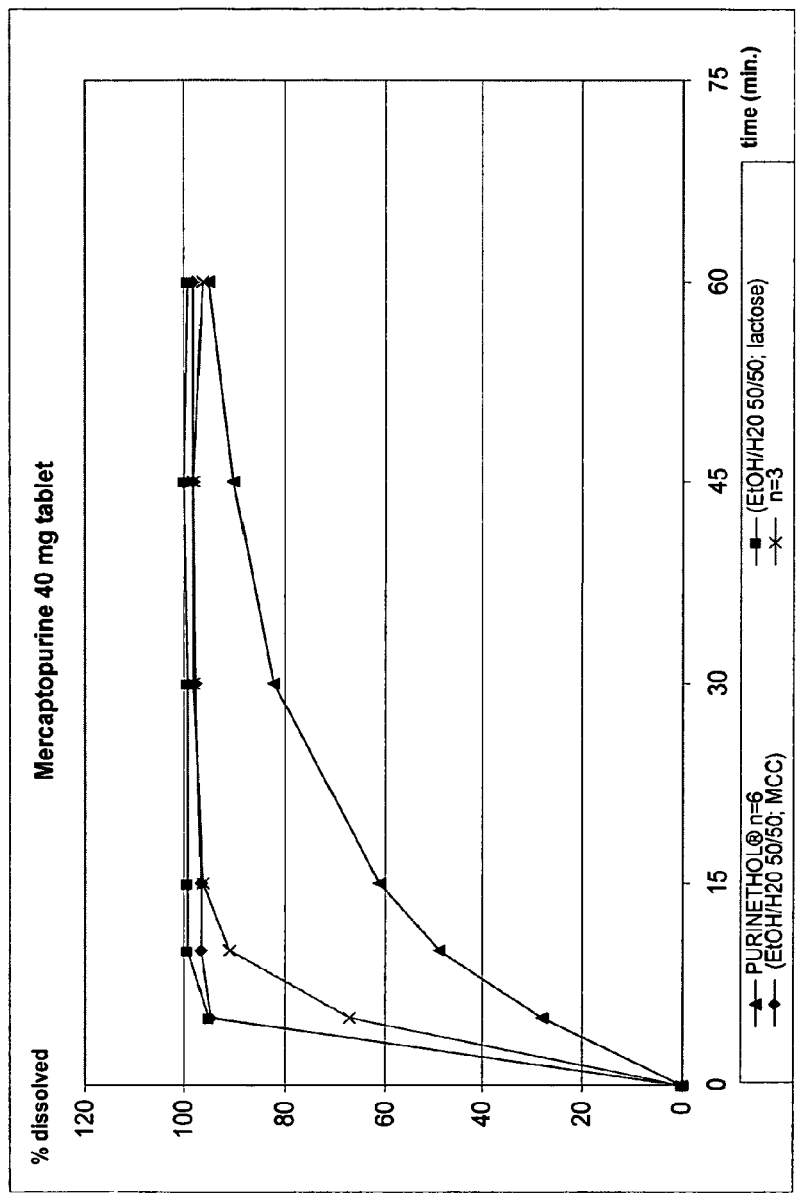
FIG. 4 shows the dissolution of a 6-mercaptopurine tablets prepared as in Example 3. -▲-=PURINETHOL®; -♦-=tablets prepared with microcrystalline cellulose; -■-=tablets prepared with lactose; -x-=lactose tablets, 70% ethanol, 30% water, n=3 (average of three tablets).

The results of the dissolution of 6-MP tablets prepared as in this example in 900 ml 0.1 N HCl at 37° C. and 50 rpm is shown in FIG. 4.

Example 4

A Comparative Bioavailability Study of a New Oral Formulation of 6-Mercaptopurine (6-MP-IB) vs. PURINETHOL® in Beagle Dogs Study Objective—

To determine the pharmacokinetic profile (AUCt and $AUC_I$, Cmax, Tmax, and half life of 6-mercaptopurine in the plasma following oral ingestion of each formulation to show improved bioavailability for 6-MP-IB Study Design—

Single center, single dose, non-randomized, open label (blinded to analyst), two treatment, two period crossover comparative bioavailability study.

Subjects—

Six female beagle dogs, 2-3 years old, 9-11 kg body weight.

Study Administrations

1) PURINETHOL® (GSK): Half of a 50 mg tablet (i.e. 25 mg) of 6-mercaptopurine, Lot #A067350.

2) 6-MP-IB batch 131-018-6: Half of a 50 mg tablet (i.e. 25 mg) of 6-mercaptopurine.

The dogs received the half tablets in the fasted state (twelve hours fast). The tablets were placed in the back of the dog's throat. About 10 ml of water was squirted into the mouth with a syringe to facilitate swallowing. The mouth was examined to ensure that the tablet was swallowed.

Blood Collection and Handling

Blood samples were taken from an indwelling catheter inserted in the jugular vein at 0 hour and at 0.25, 0.5, 1.0, 1.5, 2.0, 3.0, 4.0, 5.0, and 6.0 hours post dosing. Seven milliliters of blood was collected at each time point. The blood was chilled in ice immediately after collection. Within two minutes of collection the blood was transferred to tubes containing EDTA. The blood was processed to obtain the plasma within one hour. The plasma was stabilized with dithiothreitol and frozen to −80° C.

Analyses

The analysis of 6-MP in the plasma was carried out at Anapharm Laboratories by a validated LC/MS/MS method.

Study Duration

Two study sessions with a wash out of two weeks between study sessions.

Results

The results of the analysis of 6-MP in the plasma for all the dogs are given in Table 4A for the reference PURINETHOL® and in Table 4B for the test formulation 6-MP-IB.

The results of the calculated pharmacokinetic parameters from the concentration data are collected in Table 5 while the results of a per dog ratio analysis are given in Table 6. The average pharmacokinetic profiles for all six dogs for each treatment are given in FIG. 3.

One can see in Table 5 that the average AUCt and $AUC_I$ are both about 20% higher for the test formulation (i.e., the composition of the present invention) when compared to the standard formulation. The Cmax is almost 70% higher. In the ratio analysis, shown in Table 6, where each dog is its own control, there is an average ratio of 1.26 or a 26% rise in the bioavailability of the test versus the reference product.

Figure 3:
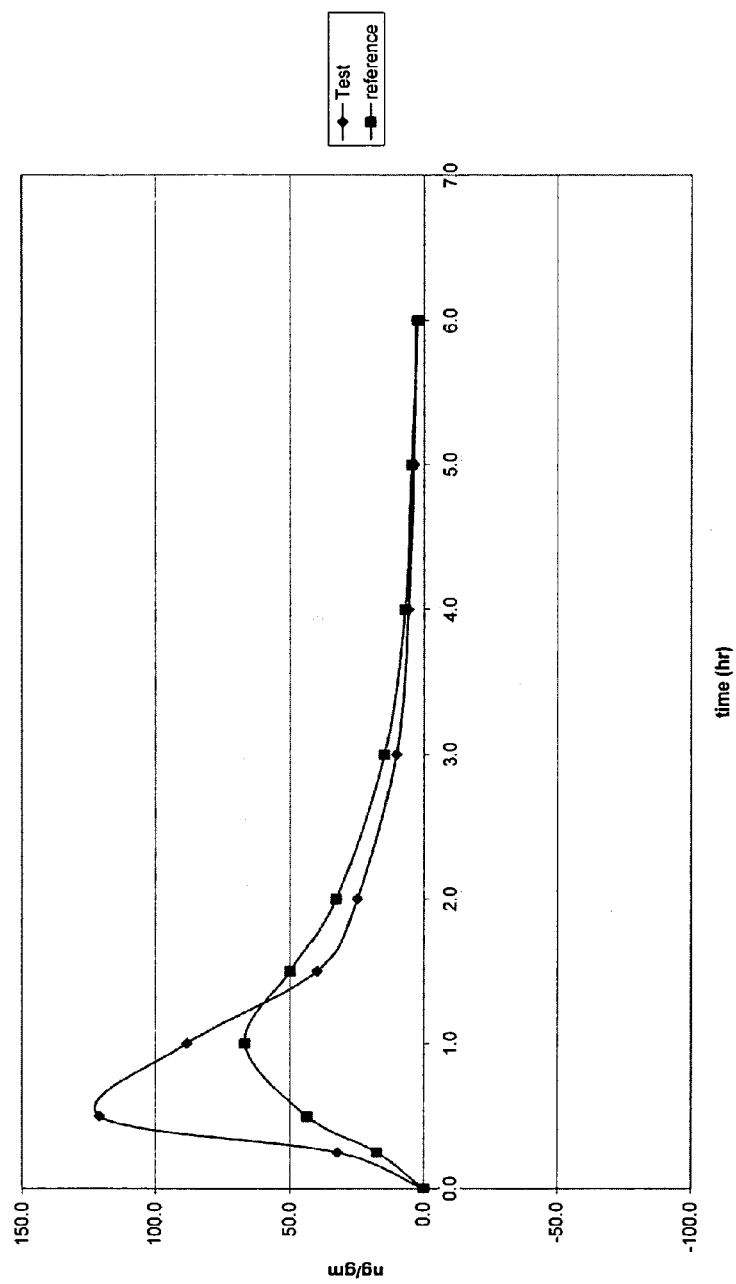
FIG. 3 shows the average pharmacokinetic profile of 6-mercaptopurine for a pharmaceutical composition of the present invention (6-MP-IB batch) vs. the standard formulation (PURINETHOL®) (see Example 4).

FIG. 3 shows that the advantage of the faster dissolving formulation in bioavailability is in the early time points with higher drug concentrations being found shortly after drug ingestion. The Tmax for the averaged data is shorter for the test compared to reference despite the fact that the average Tmax (averaged over the individual dogs) is the same for the two formulations.

CONCLUSIONS

The formulation provided by the present invention has been shown to give a more than 20% increase in bioavailability of 6-mercaptopurine in vivo when compared to an equivalent dose of the standard formulation. The improved bioavailability is expected to allow improved therapeutic outcomes.

TABLE 5

Pharmokinetic results of dog study of 6-Mercaptopurine

| Dog-session-treatment | AUCt (h*ng/g) | AUCi (h*ng/g) | t½ (h) | Tmax (h) | Cmax (ng/g) |
|---|---|---|---|---|---|
| 02 - 2- test | 235.8 | 241.7 | 1.1 | 1.0 | 181.6 |
| 03 - 2- test | 220.2 | 220.2 | 0.9 | 0.5 | 159.5 |
| 04 -2 - test | 176.1 | 188.2 | 1.0 | 0.5 | 173.8 |
| 05 - 2 - test | 324.4 | 338.5 | 1.7 | 1.0 | 380.7 |
| 06 - 2- test | 154.7 | 160.6 | 1.0 | 1.0 | 105.0 |
| 11 - 2- test | 143.6 | 143.6 | 0.9 | 0.5 | 139.6 |
| 02- 1- ref | 272.6 | 279.5 | 0.9 | 1.0 | 149.7 |
| 03 - 1- ref | 120.7 | 124.5 | 1.0 | 0.5 | 53.2 |
| 04 - 1 - ref | 130.0 | 130.0 | 1.7 | 0.5 | 112.9 |
| 05 - 1- ref | 217.3 | 224.3 | 1.0 | 1.0 | 123.1 |
| 06 - 1 - ref | 179.8 | 183.3 | 1.1 | 0.5 | 143.8 |
| 11 - 1 - ref | 124.0 | 126.2 | 0.8 | 1.5 | 91.8 |
| AVG(test) | 209.1 | 215.5 | 1.1 | 0.8 | 190.0 |
| AVG (ref) | 174.1 | 178.0 | 1.1 | 0.8 | 112.4 |

TABLE 6

Ratio Analysis

| Dog | Cmaxtest/Cmaxref | AUCt-test/AUCt-ref |
|---|---|---|
| 02 | 1.21 | 0.86 |
| 03 | 3.00 | 1.82 |
| 04 | 1.54 | 1.35 |
| 05 | 3.09 | 1.49 |
| 06 | 0.73 | 0.86 |
| 11 | 1.52 | 1.16 |
| AVG | 1.848 | 1.259 |

What is claimed is:

1. A method of treatment of a subject afflicted with Crohn's disease which results in an improved side effect profile as compared to treatment of a subject afflicted by Crohn's disease by a standard formulation of 6-mercaptopurine (6-MP), the method comprising orally administering to the subject a compressed tablet consisting of 6-MP and one or more phar- TABLE 4a 6-mercaptopurine standard formulation (PURINETHOL ®) concentrations (ng/ml)

| Subject # | Period # | Draw Times (Hour) | | | | | | | | | |
|---|---|---|---|---|---|---|---|---|---|---|---|
| | | 0.000 | 0.250 | 0.500 | 1.00 | 1.50 | 2.00 | 3.00 | 4.00 | 5.00 | 6.00 |
| 02 | 1 | <2.00 | 35.15 | 38.98 | 149.72 | 131.27 | 80.36 | 26.90 | 11.01 | 7.87 | 5.37 |
| 03 | 1 | <2.00 | <2.00 | 53.24 | 41.64 | 31.96 | 39.83 | 19.10 | 8.85 | 4.76 | 2.73 |
| 04 | 1 | <2.00 | 21.69 | 112.90 | 54.94 | 26.45 | 15.24 | 9.75 | 12.12 | 8.24 | <2.00 |
| 05 | 1 | <2.00 | 20.97 | <2.00 | 123.11 | 75.23 | 62.88 | 41.19 | 13.16 | 8.96 | 4.87 |
| 06 | 1 | <2.00 | 61.09 | 143.83 | 106.22 | 42.88 | 22.53 | 8.98 | 5.84 | 3.23 | 2.19 |
| 11 | 1 | <2.00 | <2.00 | <2.00 | 59.72 | 91.79 | 39.99 | 10.20 | 4.53 | 2.46 | 2.03 |

TABLE 4b 6-mercaptopurine (6-MP-IB 131-018-6) concentrations (ng/ml)

| Subject # | Period # | Draw Times (Hour) | | | | | | | | | |
|---|---|---|---|---|---|---|---|---|---|---|---|
| | | 0.000 | 0.250 | 0.500 | 1.00 | 1.50 | 2.00 | 3.00 | 4.00 | 5.00 | 6.00 |
| 02 | 2 | <2.00 | 25.07 | 109.97 | 181.60 | 77.10 | 37.32 | 15.22 | 8.52 | 5.29 | 3.83 |
| 03 | 2 | <2.00 | 129.92 | 159.49 | 79.27 | 77.05 | 37.12 | 11.66 | 6.64 | 3.62 | <2.00 |
| 04 | 2 | <2.00 | 30.68 | 173.75 | 99.24 | 35.45 | 21.17 | 8.88 | 4.35 | 2.71 | 8.29 |
| 05 | 2 | <2.00 | <2.00 | 380.69 | 172.31 | 59.78 | 27.99 | 20.85 | 12.50 | 8.26 | 5.91 |
| 06 | 2 | <2.00 | <2.00 | 4.61 | 104.99 | 44.09 | 53.45 | 19.34 | 10.30 | 6.69 | 4.05 |
| 11 | 2 | <2.00 | 70.75 | 139.59 | 69.21 | 24.87 | 21.03 | 5.47 | 3.15 | 2.14 | <2.00 | maceutical carriers, which compressed tablet exhibits enhanced solubility in aqueous acid compared to the standard formulation of 6-MP and provides to the subject a therapeutic outcome with an improved side effect profile as compared to the treatment by the standard formulation of 6-MP.

2. The method of claim 1, wherein the compressed tablet comprises 0.5 mg to 150 mg of 6-MP.

3. The method of claim 2, wherein the compressed tablet comprises 40 mg of 6-MP.

4. The method of claim 2, wherein the compressed tablet comprises 50 mg of 6-MP.

5. The method of claim 1, wherein the dose of 6-MP administered by the compressed tablet is at least 15% less than the dose administered by the standard formulation.

6. The method of claim 1, wherein the dose administered by the compressed tablet achieves the same bioavailability as the standard formulation.

7. A method of improving the side effect profile of a treatment of a subject afflicted by Crohn's disease by a standard formulation of 5-mercaptopurine (6-MP), which method comprises orally administering to the subject a compressed tablet consisting of an amount of 6-MP sufficient to result in a therapeutic outcome and one or more pharmaceutical carriers, which compressed tablet exhibits enhanced solubility in aqueous acid compared to the standard formulation of 6-MP, thereby treating the subject with an improved side effect profile.

8. The method of claim 7, wherein the compressed tablet comprises 0.5 mg to 150 mg of 6-MP.

9. The method of claim 8, wherein the compressed tablet comprises 40 mg of 6-MP.

10. The method of claim 8, wherein the compressed tablet comprises 50 mg of 6-MP.

11. The method of claim 7, wherein the dose of 6-MP administered by the compressed tablet is at least 15% less than the dose administered by the standard formulation.

12. The method of claim 11, wherein the dose administered by the compressed tablet achieves the same bioavailability as the standard formulation.

\* \* \* \* \*